(12) United States Patent
Ziskind et al.

(10) Patent No.: US 11,446,116 B2
(45) Date of Patent: Sep. 20, 2022

(54) METHOD AND APPARATUS FOR DENTAL CROWN RESTORATIONS USING PREFABRICATED SLEEVE-CROWN PAIRS

(71) Applicant: PERFECT FIT CROWNS, LLC, Elkton, MD (US)

(72) Inventors: Stephen A. Ziskind, Lexington, KY (US); Edwin Michael First, Prescott Valley, AZ (US); Adam Szeremeta, Mission Viejo, CA (US); Robin A. Carden, San Juan Capistrano, CA (US)

(73) Assignee: PERFECT FIT CROWNS, LLC, Elkton, MD (US)

( * ) Notice: Subject to any disclaimer, the term of this patent is extended or adjusted under 35 U.S.C. 154(b) by 0 days.

(21) Appl. No.: 17/367,873

(22) Filed: Jul. 6, 2021

(65) Prior Publication Data
US 2022/0000582 A1   Jan. 6, 2022

Related U.S. Application Data

(60) Provisional application No. 63/048,569, filed on Jul. 6, 2020, provisional application No. 63/048,558, filed
(Continued)

(51) Int. Cl.
*A61C 5/73* (2017.01)
*A61C 13/08* (2006.01)
(Continued)

(52) U.S. Cl.
CPC ............ *A61C 5/73* (2017.02); *A61C 5/30* (2017.02); *A61C 8/0016* (2013.01); *A61C 13/01* (2013.01); *A61C 13/081* (2013.01); *A61C 13/082* (2013.01); *A61C 13/083* (2013.01); *A61C 13/087* (2013.01); *A61C 13/10* (2013.01); *A61C 13/206* (2013.01); *A61K 6/15* (2020.01); *A61K 6/30* (2020.01); *A61K 6/884* (2020.01)

(58) Field of Classification Search
CPC .... A61C 5/30; A61C 5/70; A61C 5/73; A61C 13/0001; A61C 13/08; A61C 13/087; A61C 13/34
See application file for complete search history.

(56) References Cited

U.S. PATENT DOCUMENTS 2,770,040 A   11/1956 Moyer
2,930,124 A   3/1960 Pos
(Continued)

FOREIGN PATENT DOCUMENTS

EP    3610824   *  2/2020
WO    WO 2011/059561   5/2011

OTHER PUBLICATIONS

International Search Report dated Jan. 31, 2022 for International Application Serial No. PCT/US31/40527.

*Primary Examiner* — Edward Moran
(74) *Attorney, Agent, or Firm* — F. Chau & Associates, LLC

(57) ABSTRACT

A dental restoration device includes a sleeve having an exterior surface and an interior pocket that is at least partially filled with a dental cement, and a crown having an exterior surface and an interior surface that is mated to the exterior surface of the crown and bonded thereto by an adhesive disposed between the exterior surface of the sleeve and the interior surface of the crown.

26 Claims, 32 Drawing Sheets

Related U.S. Application Data on Jul. 6, 2020, provisional application No. 63/048,551, filed on Jul. 6, 2020, provisional application No. 63/122,742, filed on Dec. 8, 2020.

(51) Int. Cl.

| | | |
|---|---|---|
| *A61C 13/083* | (2006.01) | |
| *A61C 5/30* | (2017.01) | |
| *A61K 6/884* | (2020.01) | |
| *A61C 8/00* | (2006.01) | |
| *A61C 13/01* | (2006.01) | |
| *A61C 13/20* | (2006.01) | |
| *A61K 6/30* | (2020.01) | |
| *A61C 13/087* | (2006.01) | |
| *A61C 13/10* | (2006.01) | |
| *A61K 6/15* | (2020.01) | |

(56) References Cited

U.S. PATENT DOCUMENTS

| | | |
|---|---|---|
| 3,058,216 A | 10/1962 | Cohen |
| 3,521,357 A | 7/1970 | Berglund et al. |
| 3,881,251 A | 5/1975 | Valen |
| 4,206,545 A | 6/1980 | Lord |
| 4,332,564 A | 6/1982 | Lord |
| 4,398,887 A | 8/1983 | Balde et al. |
| 4,504,230 A | 3/1985 | Patch |
| 4,575,340 A | 3/1986 | Lustig |
| 4,678,435 A | 7/1987 | Long |
| 4,710,127 A | 12/1987 | Bellavia et al. |
| 4,834,656 A | 5/1989 | Loudon |
| 4,838,790 A | 6/1989 | Koller |
| 5,314,335 A | 5/1994 | Fung |
| 5,458,489 A | 10/1995 | Tennyson |
| 5,487,663 A | 1/1996 | Wilson |
| 5,775,913 A | 7/1998 | Updyke et al. |
| 5,869,548 A | 2/1999 | Ikushima et al. |
| 5,885,077 A | 3/1999 | Jeffer |
| 5,948,129 A | 9/1999 | Nonami et al. |
| 6,063,830 A | 5/2000 | Deguchi et al. |
| 6,068,481 A | 5/2000 | Worthington |
| 6,147,136 A | 11/2000 | Bissinger |
| 6,183,256 B1 | 2/2001 | Fisher et al. |
| 6,250,926 B1 | 6/2001 | Foser et al. |
| 6,325,629 B1 | 12/2001 | Fisher et al. |
| 6,384,107 B2 | 5/2002 | Liu |
| 6,444,597 B1 | 9/2002 | Sato et al. |
| 6,592,373 B2 | 7/2003 | Zilberman |
| 6,599,125 B1 | 7/2003 | Freilich et al. |
| 6,653,365 B2 | 11/2003 | Jia |
| 6,663,387 B2 | 12/2003 | Riley |
| 6,852,775 B1 | 2/2005 | Soglowek et al. |
| 6,884,073 B2 | 4/2005 | Chilibeck |
| 6,921,500 B1 | 7/2005 | Feenstra |
| 6,935,862 B2 | 8/2005 | Harlan |
| 6,955,540 B2 * | 10/2005 | Mayer ................. A61K 6/891 |
| | | 433/172 |
| 6,955,776 B1 | 10/2005 | Feenstra |
| 7,008,229 B2 | 3/2006 | Stoller et al. |
| 7,160,941 B2 | 1/2007 | Jin et al. |
| 7,241,856 B2 | 7/2007 | Jin et al. |
| 7,494,339 B2 | 2/2009 | Dias et al. |
| 7,589,132 B2 | 9/2009 | Jia et al. |
| 7,632,877 B2 | 12/2009 | Jin et al. |
| 7,662,869 B2 | 2/2010 | Bissinger et al. |
| 7,674,580 B2 | 3/2010 | Saba et al. |
| 7,700,666 B2 | 4/2010 | Bissinger et al. |
| 7,925,374 B2 | 4/2011 | Andersson et al. |
| 7,977,404 B2 | 7/2011 | Wolter et al. |
| 8,329,776 B2 | 12/2012 | Hecht et al. |
| 8,338,503 B2 | 12/2012 | Ando |
| 8,389,598 B2 | 3/2013 | Saimi et al. |
| 8,445,558 B2 | 5/2013 | Karim et al. |
| 8,466,210 B2 | 6/2013 | Zech et al. |
| 8,466,212 B2 * | 6/2013 | Moszner ................. A61K 6/891 |
| | | 106/35 |
| 8,552,086 B2 | 10/2013 | Karim et al. |
| 8,636,512 B2 * | 1/2014 | Dierkes ................. A61C 5/77 |
| | | 433/201.1 |
| 8,636,928 B2 | 1/2014 | Sun et al. |
| 8,651,867 B2 | 2/2014 | Zilberman |
| 8,686,061 B2 | 4/2014 | Neffgen et al. |
| 8,710,113 B2 | 4/2014 | Eckert et al. |
| 8,853,338 B2 | 10/2014 | Wang et al. |
| 8,865,033 B2 | 10/2014 | Schechner |
| 9,119,692 B2 | 9/2015 | Sun et al. |
| 9,138,382 B2 | 9/2015 | Moszner et al. |
| 9,168,206 B2 | 10/2015 | Wang et al. |
| 9,295,617 B2 | 3/2016 | Eckert et al. |
| 9,314,408 B2 | 4/2016 | Blomker et al. |
| 9,333,150 B2 | 5/2016 | Moszner et al. |
| 9,381,140 B2 | 7/2016 | Bublewitz et al. |
| 9,403,726 B2 | 8/2016 | Fischer et al. |
| 9,532,931 B2 | 1/2017 | Lubbe |
| 9,764,982 B2 | 9/2017 | Ritzberger et al. |
| 9,782,329 B2 | 10/2017 | Hecht et al. |
| 9,833,388 B2 | 12/2017 | Willner et al. |
| 9,855,195 B2 | 1/2018 | Takahashi et al. |
| 9,856,165 B2 | 1/2018 | Theocharopoulos et al. |
| 10,004,669 B2 | 6/2018 | Eckert et al. |
| 10,010,488 B2 | 7/2018 | Eckert et al. |
| 10,028,805 B2 | 7/2018 | Tairaku |
| 10,080,629 B2 | 9/2018 | McDonald et al. |
| 10,085,923 B2 | 10/2018 | Nakatsuka et al. |
| 10,098,985 B2 | 10/2018 | Sereno et al. |
| 10,125,054 B2 * | 11/2018 | Lee ................. C04B 35/64 |
| 10,131,569 B2 | 11/2018 | Krolikowski et al. |
| 10,157,330 B2 | 12/2018 | Azernikov et al. |
| 10,248,885 B2 | 4/2019 | Nikolskiy et al. |
| 10,376,343 B2 | 8/2019 | Rheinberger et al. |
| 10,377,661 B2 | 8/2019 | Rampf et al. |
| 10,391,039 B2 | 8/2019 | Takeuchi et al. |
| 10,442,725 B2 | 10/2019 | Durschang et al. |
| 10,457,589 B2 | 10/2019 | Rampf et al. |
| 10,501,366 B2 | 12/2019 | Ritzberger et al. |
| 10,610,330 B2 | 4/2020 | Herrmann et al. |
| 10,614,174 B2 | 4/2020 | Lee et al. |
| 2002/0106610 A1 | 8/2002 | Hurson |
| 2003/0194681 A1 | 10/2003 | Stoller et al. |
| 2003/0203339 A1 * | 10/2003 | Chilibeck ................. A61C 5/30 |
| | | 433/226 |
| 2004/0036178 A1 | 2/2004 | Mayer et al. |
| 2004/0152049 A1 | 8/2004 | Cornelissen |
| 2004/0161726 A1 * | 8/2004 | Saito ................. A61C 5/73 |
| | | 433/222.1 |
| 2005/0282110 A1 | 12/2005 | Goodman et al. |
| 2006/0040238 A1 | 2/2006 | Mannia |
| 2006/0099549 A1 | 5/2006 | Engman |
| 2006/0118790 A1 | 6/2006 | Alon et al. |
| 2006/0154211 A1 | 7/2006 | Bybee et al. |
| 2007/0003908 A1 | 1/2007 | Porter |
| 2007/0020682 A1 | 1/2007 | Neumeyer |
| 2007/0031792 A1 | 2/2007 | Casement et al. |
| 2007/0031793 A1 | 2/2007 | Casement et al. |
| 2007/0059662 A1 | 3/2007 | Bittar |
| 2007/0072162 A1 | 3/2007 | Jaghab |
| 2007/0093188 A1 | 4/2007 | Nemoto |
| 2007/0141535 A1 | 6/2007 | Baldissara |
| 2007/0184412 A1 | 8/2007 | Borowski et al. |
| 2007/0196792 A1 | 8/2007 | Johnson et al. |
| 2008/0008981 A1 | 1/2008 | Groll et al. |
| 2008/0026345 A1 | 1/2008 | Jaklinski et al. |
| 2008/0032266 A1 | 2/2008 | Harlass |
| 2008/0085490 A1 | 4/2008 | Jabri |
| 2009/0017420 A1 | 1/2009 | Jabri |
| 2009/0117517 A1 | 5/2009 | Koster |
| 2009/0123888 A1 * | 5/2009 | Rosenberg ............ A61C 8/0048 |
| | | 433/173 |
| 2009/0319038 A1 | 12/2009 | Sager |
| 2010/0003641 A1 | 1/2010 | Hansen et al. |
| 2010/0021868 A1 | 1/2010 | Kvitrud et al. |
| 2010/0028835 A1 | 2/2010 | Hansen et al. |
| 2010/0047740 A1 | 2/2010 | Fyffe |

(56) References Cited

U.S. PATENT DOCUMENTS

| | | |
|---|---|---|
| 2010/0092910 A1 | 4/2010 | Machado et al. |
| 2010/0203480 A1* | 8/2010 | Schweitzer ............ A61C 5/77 433/223 |
| 2010/0216092 A1 | 8/2010 | Garcia Saban et al. |
| 2011/0117524 A1* | 5/2011 | McDonald ............ A61C 5/70 433/218 |
| 2011/0207087 A1* | 8/2011 | Jones ............ A61C 13/20 433/222.1 |
| 2011/0300509 A1 | 12/2011 | Dadi |
| 2012/0141956 A1 | 6/2012 | Mandell |
| 2012/0156650 A1* | 6/2012 | Glidewell ............ A61C 13/09 433/223 |
| 2012/0175890 A1 | 7/2012 | Rupert et al. |
| 2013/0085199 A1 | 3/2013 | Morehead |
| 2013/0209961 A1* | 8/2013 | Rubbert ............ A61C 8/0036 433/175 |
| 2013/0309628 A1 | 11/2013 | Orth et al. |
| 2014/0113250 A1* | 4/2014 | Beveridge ............ A61C 19/10 433/219 |
| 2014/0234799 A1 | 8/2014 | Lim |
| 2014/0297015 A1 | 10/2014 | Sager |
| 2015/0374463 A1 | 12/2015 | Sager |
| 2016/0022378 A1 | 1/2016 | Hansen et al. |
| 2016/0030142 A1 | 2/2016 | Haas |
| 2016/0157967 A1 | 6/2016 | Kim et al. |
| 2016/0184189 A1 | 6/2016 | Hagiwara et al. |
| 2016/0346066 A1 | 12/2016 | Wang |
| 2017/0028179 A1 | 2/2017 | Ou |
| 2017/0172706 A1 | 6/2017 | Lapinski et al. |
| 2017/0196665 A1 | 7/2017 | Sager |
| 2017/0249418 A1 | 8/2017 | Sager |
| 2017/0268553 A1 | 9/2017 | Hansen et al. |
| 2017/0300813 A1 | 10/2017 | Sager |
| 2018/0064518 A1 | 3/2018 | Sutera, III |
| 2018/0214253 A1 | 8/2018 | Guerra |
| 2019/0021815 A1 | 1/2019 | Herrmann et al. |
| 2019/0110864 A1 | 4/2019 | Clunet-Coste et al. |
| 2020/0107913 A1 | 4/2020 | Yahav |
| 2020/0146787 A1 | 5/2020 | Metsger |
| 2020/0205935 A1 | 7/2020 | Herrmann et al. |
| 2020/0206092 A1 | 7/2020 | Herrmann et al. |
| 2021/0177544 A1* | 6/2021 | Vollmann ............ A61C 5/73 |

* cited by examiner

FIG. 17

| Material type | Materials (Code) | Composition by weight | | Manufacturer |
|---|---|---|---|---|
| | | Filler | polymer | |
| Resin composite CAD CAM blocks | Lava™ Ultimate (LU) | 80% silica and zirconia nano particles | 20% ( Bis-GMA, UDMA, Bis-EMA, TEGDMA) | 3M™ESPE™ USA |
| | Shofu (SH) | 61% Silica-based glass and silica | UDMA+TEGDMA | Shofu |
| | Cerasmart (CS) | 71% Silica and barium glass nanoparticles | Bis-MEPP, UDMA, DMA | GC dental products, Europe |
| | BRILLIANT Crios (BC) | 70% of glass and amorphous silica | Cross-linked methacrylates (Bis-GMA, Bis-EMA, TEGDMA) | COLTENE, Switzerland |
| | Grandio Blocs (GR) | 86% Nanohybrid fillers | 14% UDMA+ DMA | VOCO GmbH |
| Polymer infiltrated ceramic network (PICN) ceramic | Vita Enamic (EN) | 86% ceramic | 14% UDMA+TEGDMA | Vita Zahnfabrik, Germany |
| Pure PEEK | Ceramill PEEK (PE) | 0 | 100% PEEK | Juvora, UK |
| Ceramic filled PEEK | Dentokeep (DK) | 20% TiO$_2$ | 80% PEEK | Nt-trading Germany |
| Feldspathic ceramic block | Vitablocs Mark II (VM) | Fine-particle feldspar ceramic | 0 | Vita Zahnfabrik, Germany |

FIG. 18

| Material type | Material (code) | Microhardness (Kg/mm²) | Nanohardness (GPa) | Elastic Modulus (GPa) | Manufacturers' Filler (wt%) | measured filler (wt%) |
|---|---|---|---|---|---|---|
| Resin composite CAD/CAM blocks | Lava™-Ultimate (LU) | 112.6 (0.44) | 1.25 (0.05) | 12.14 (0.26) | 80 | 78.8 (0.1) |
| | Shofu (SH) | 73.12 (1.04) | 0.775 (0.03) | 8.29 (0.35) | 61 | 63 (0.02) |
| | Cerasmart (CS) | 80.06 (0.76) | 0.81 (0.006) | 10.36 (0.17) | 70 | 66.1 (0.2) |
| | BRILLIANT Crios (BC) | 82.61 (0.49) | 0.85 (0.008) | 10.88 (0.6) | 71 | 70.1 (0.05) |
| | Grandio Blocs (GR) | 121.8 (2.1) | 1.3 (0.05) | 14.8 (0.4) | 86 | 84.6 (0.03) |
| Polymer infiltrated ceramic network (PICN) ceramic | Vita Enamic (EN) | 203.1 (0.43) | 3.1 (0.17) | 34.56 (1.4) | 86 | 85.1 (0.1) |
| Pure PEEK | Ceramill PEEK (PE) | 25.7 (0.05) | 0.317 (0.006) | 2.53 (0.15) | 0 | .00 (0) |
| Ceramic filled PEEK | Dentokeep (DK) | 27.74 (0.19) | 0.34 (0.03) | 3.43 (0.29) | 20 | 27.3 (0.06) |
| Feldspathic ceramic Block | Vitablocs Mark II (VM) | 502.4 (2.28) | 6.83 (0.379) | 47.7 (3.47) | 100 | 100 (0) |
| Enamel | EM | 313.3 (22.7) | 4.03 (0.35) | 59.7 (11) | - | - |
| Dentine | DN | 62.3 (3.3) | 0.76 (0.13) | 16.5 (2.3) | - | - |

FIG. 19

FIG. 28
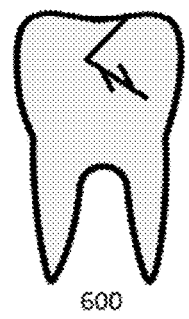
600
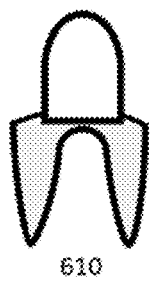
610
620
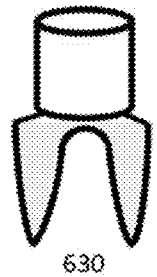
630
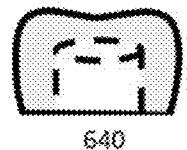
640
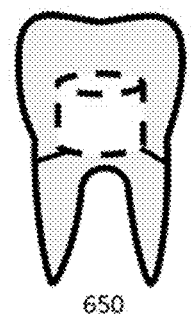
650
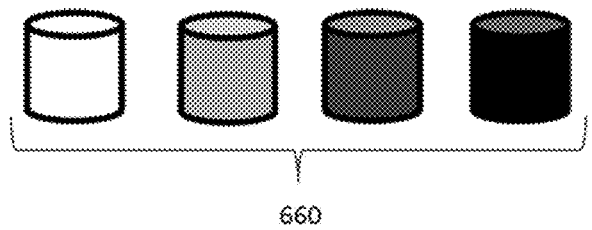
660

METHOD AND APPARATUS FOR DENTAL CROWN RESTORATIONS USING PREFABRICATED SLEEVE-CROWN PAIRS

CROSS-REFERENCE TO RELATED APPLICATION

The present application is based on provisional patent application Ser. No. 63/048,569, filed on Jul. 6, 2020; provisional patent application Ser. No. 63/048,558, filed on Jul. 6, 2020; provisional patent application Ser. No. 63/048,551, filed on Jul. 6, 2020; and provisional patent application Ser. No. 63/122,742, filed on Dec. 8, 2020, the entire contends of which are herein incorporated by reference.

TECHNICAL FIELD

The present disclosure relates to dental crown restorations and, more specifically, to methods and apparatuses for dental crown restorations using prefabricated sleeve-crown pairs.

DISCUSSION OF THE RELATED ART

A dental crown is a dental restoration that is installed over a natural tooth or dental implant so as to provide a restored functional surface and a natural and healthy aesthetic appearance. Prior to applying a dental crown to a natural tooth, the tooth is first prepared by grinding down the affected tooth to a peg or post-shaped element that is free of disease and is structurally sound. Thereafter, intra-oral digital scans, measurements and/or impressions of the teeth are taken and the coloring of the surrounding teeth is measured. This information is provided to a lab that fabricates a crown that is customized to the shape of the prepared tooth, the ideal final shape of the prepared tooth, the spacing of the mouth and teeth around the prepared tooth, and the color of the surrounding teeth.

Custom fabrication of the crown, however, is time consuming and expensive and requires that the patient be brought in on multiple occasions. On a first visit, the patient may consult with the dentist and a course of treatment may be determined. On this visit or on a second visit, the affected tooth may be prepared and impressions may be taken. A temporary crown may then be installed on the prepared tooth. If the temporary crown falls out prior to the installation of the permanent crown, which is not unusual, then an emergency visit to the dentist's office for repair or replacement may be required. After the final crown is custom fabricated, the patient returns to the dentist's office to have the temporary crown removed and the custom crown installed. If the custom crown fails to fit properly during installation, which may be possible if a bad impression was taken or the crown was made improperly by the lab, additional time is required to replace the custom crown, the patient may require a new temporary crown and another visit to place the replacement crown. Similar problems may occur if the color of the crown does not match that of the surrounding teeth. It is also possible for the prepared tooth to change position in the time between the preparing of the tooth and the installation of the custom crown, as the prepared tooth no longer has the constant opposing force of the opposite teeth. This change in position may cause the custom crown to either not fit or fit awkwardly, requiring trimming or polishing during installation, or in extreme cases, the need for a new crown to be made.

One option for providing single-visit dental crowns is in-office/chairside milling. According to this approach, an intraoral scanning device is used to image the patient's mouth with the prepared tooth. The image is then sent to a local workstation where the design for the crown can be customized and approved. From there, the digital design is sent to a chairside mill that automatically grinds out the crown based on the design. The crown may then be prepared, directly pigmented, glazed, and polished and then its fit may be tested in the patient's mouth. The crown may then be installed in the patient's mouth in that same visit.

While chairside milling may be effective at reducing the number of visits needed to perform the restoration, this approach is time consuming (it could take more than 90 minutes to perform chairside milling), requires significant training of the dentist and dental staff, and requires significant capital investment on the part of the treating dentist.

SUMMARY

A dental restoration device includes a sleeve having an exterior surface and an interior pocket that is at least partially filled with a dental cement, and a crown having an exterior surface and an interior surface that is mated to the exterior surface of the sleeve and bonded thereto by an adhesive disposed between the exterior surface of the sleeve and the interior surface of the crown.

A method for installing a dental restoration includes preparing an affected tooth of a patient by removing diseased and/or damaged matter so as to achieve a substantially post-shaped prepared tooth, determining a desired crown shape based on a size and/or spacing of the patient's mouth and a type of the affected tooth, determining a desired tooth color based on observing a color of teeth proximate to the affected tooth, selecting a prefabricated crown in accordance with the determined crown shape and determined desired tooth color, from among a kit of prefabricated crowns of different sizes and colors, the selected prefabricated crown being associated with a prefabricated sleeve, filling an interior pocket of the associated prefabricated sleeve with dental cement, placing the filled sleeve with the crown disposed thereon over the prepared tooth, pressing the filled sleeve to a desired position with respect to a gum line of the patient by the patient biting down on the crown, removing the crown from the sleeve, curing the dental cement with a light source that is cast through the sleeve, and bonding the interior surface of the crown to the exterior surface of the sleeve using an adhesive.

A kit of prefabricated dental crowns includes a plurality of prefabricated dental crowns organized by tooth type, size, and shade, and a plurality of sleeves, each of which is associated with a corresponding crown of the plurality of prefabricated dental crowns. Each of the plurality of sleeves has an exterior surface that is shaped to mate with an interior surface of the corresponding crown of the plurality of prefabricated dental crowns, and each of the plurality of sleeves is at least partially translucent to light of a particular spectrum.

A method for providing dental drilling guidance includes acquiring intraoral image data of a patient's dental arch, acquiring x-ray image data of the patient's dental arch, registering the acquired intraoral image data and the acquired x-ray image data to a combined 3D model, segmenting a region of diseased tissue of an affected tooth from the combined 3D model, computing a removal volume for the affected tooth from the combined 3D model, generating tooth preparation guidance showing where along the affected tooth drilling is to be performed, and displaying the generated tooth preparation guidance as drilling is performed.

A method for providing haptic guidance includes acquiring intraoral image data of a patient's dental arch, acquiring x-ray image data of the patient's dental arch, registering the acquired intraoral image data and the acquired x-ray image data to a combined 3D model, segmenting a region of diseased or damaged tissue of an affected tooth from the combined 3D model, computing a removal volume for the affected tooth from the combined 3D model and defining a preservation volume as a volume of the affected tooth that is not part of the removal volume, continuously acquiring intraoral image data of the patient's dental arch including a present location of the drill, registering the present location of the drill to the combined 3D model, determining when the present location of the drill comes within a predetermined distance to an interface between the removal volume and the preservation volume, and providing haptic feedback to a user of the drill when it is determined that the present location of the drill comes within the predetermined distance to the interface between the removal volume and the preservation volume.

A method for installing a dental crown restoration using prefabricated pigmented sleeves includes prepare an affected tooth of a patient by drilling away diseased and/or damaged volume so as to achieve a substantially peg-shaped prepared tooth, determining a desired crown shape based on a size and spacing of the patient's mouth and a type of the affected tooth, determining a desired tooth color based on observing a color of teeth proximate to the affected tooth, determine sleeve pigmentation according to the determined desired tooth color, determining a sleeve size based on a size of the prepared tooth and the determined desired crown shape, selecting a sleeve from a kit of prefabricated sleeves based on the determined sleeve size and determined sleeve pigmentation, selecting a crown from a kit of prefabricated crowns based on the determined desired crown shape, bonding the selected sleeve to the prepared tooth, and bonding the selected crown to the selected sleeve using a bonding agent that cures substantially transparent/translucent.

A kit of prefabricated pigmented sleeves includes a plurality of sleeves of a variety of sizes for mating to a prepared tooth of one of a plurality of different sizes, each of the variety of sleeves being disposed in one of a plurality of different shades so as to mate with a prefabricated crown that is substantially transparent/translucent using a bonding agent that cures substantially transparent/translucent such that the prefabricated crown so-mated to the selected sleeve creates an outer appearance of a desired color to match a coloring of teeth proximate to the prepared tooth.

A method for manufacturing dental crowns for use in dental restoration includes receiving intraoral scans of a plurality of subjects, analyzing the received intraoral scans to determine values for a plurality of size parameters for each received intraoral scan, determining average ratios between a first size parameter of the plurality of size parameters and at least one additional size parameter of the plurality of size parameters for a particular tooth type, determining an average first size parameter value based on the determined values for the plurality of size parameters for each received intraoral scan, determining at least one larger first size parameter value and at least one smaller first size parameter value based on a distribution of first size parameter values of the determined values for the plurality of size parameters for each received intraoral scan, enlarging each of the average first size parameter, the at least one larger first size parameter, and the at least one smaller first size parameter to produce a set of enlarged first size parameters, develop a computer aided design CAD model for each of the set of enlarged first size parameters by deforming a basic shape model for the particular tooth type to each of the set of enlarged first size parameters and the determined average ratios, and manufacturing a set of crowns according to the developed CAD models.

A kit of prefabricated crowns for use in dental restoration of a tooth of a particular tooth type includes a set of prefabricated crowns in a plurality of different sizes, wherein the set of prefabricated crowns is manufactured by receiving intraoral scans of a plurality of subjects, analyzing the received intraoral scans to determine values for a plurality of size parameters for each received intraoral scan, determining average ratios between a first size parameter of the plurality of size parameters and at least one additional size parameter of the plurality of size parameters for a particular tooth type, determining an average first size parameter value based on the determined values for the plurality of size parameters for each received intraoral scan, determining at least one larger first size parameter value and at least one smaller first size parameter value based on a distribution of first size parameter values of the determined values for the plurality of size parameters for each received intraoral scan, enlarging each of the average first size parameter, the at least one larger first size parameter, and the at least one smaller first size parameter to produce a set of enlarged first size parameters, develop a computer aided design CAD model for each of the set of enlarged first size parameters by deforming a basic shape model for the particular tooth type to each of the set of enlarged first size parameters and the determined average ratios, and manufacturing a set of crowns according to the developed CAD models.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein:

FIGS. 17-19 are tables illustrating examples of materials that may be used in the dental crowns in accordance with exemplary embodiments of the present disclosure;

FIG. 28 is a schematic diagram illustrating a diseased or damaged tooth, a prepared tooth, a sleeve, a sleeved tooth, a crown, a crowned tooth, and a set of pigmented sleeves, in accordance with exemplary embodiments of the present invention;

DETAILED DESCRIPTION OF THE DRAWINGS

Figure 1:
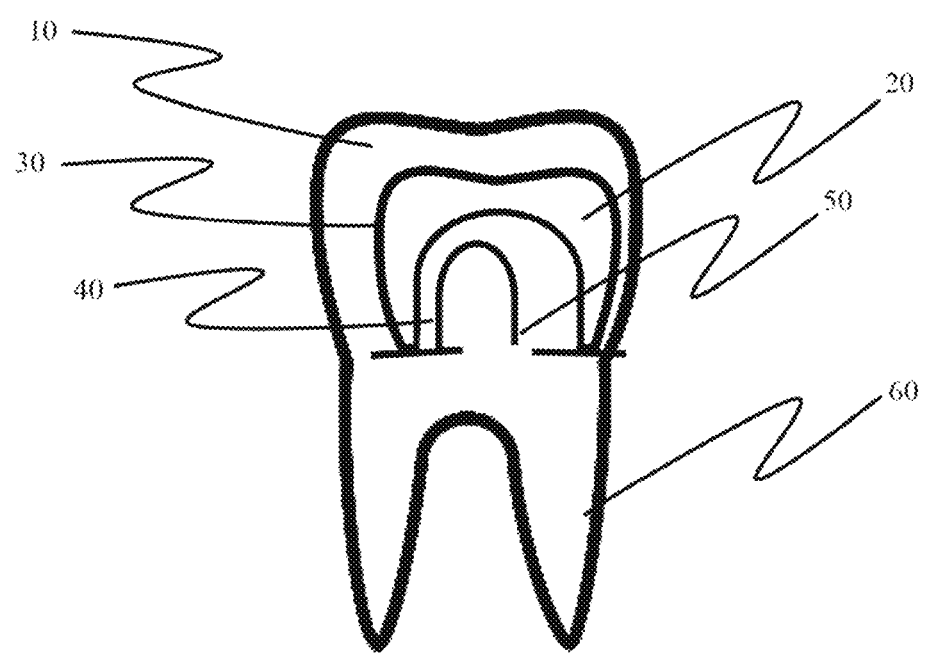
FIG. 1 is a cutaway view illustrating a prepared tooth with a sleeve-crown pair installed thereon in accordance with exemplary embodiments of the present disclosure.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

The present disclosure is organized into five main sections, namely: 1) dental crown restorations, 2) digital guidance, 3) haptic guidance, 4) colored sleeves, and 5) shaded crowns. It is to be understood, however, that each of these three sections describes aspects of a unified system for utilizing a kit of prefabricated crowns and sleeves for use in single-visit dental restorations and that each and every detail described with respect to one section of the present disclosure may be applied equally to every other section of the present disclosure. Thus, while certain details are not described repeatedly in each section, for the purpose of providing a more concise disclosure, it is to be understood that details of each section may be mixed and matched, and in particular, elements described in one section may be substituted for similar or corresponding elements described in another section.

For example, the digital guidance and haptic guidance described in sections 2 and 3 may be used as part of a method for installing the prefabricated crowns and sleeves described in section 1. For example, the concepts of the colored sleeves or shaded crowns of sections 4 and 5 could be applied to the prefabricated crowns of section 1. Additionally, all other possible combinations of features of the various sections of the disclosure are contemplated to be mix and matchable, to the greatest extent possible, without departing from the spirit and scope of the present disclosure.

Dental Crown Restorations

Exemplary embodiments of the present disclosure relate to an approach for performing a dental crown restoration in a single sitting. According to this approach, pairs of crowns and sleeves are prefabricated in a variety of different sizes and pigment shades and are added to a kit that is provided to a dentist. When a patient requires a crown, the tooth is prepped, an appropriately sized and colored crown and its associated sleeve are bonded to the prepared tooth in the manner described herein, without the patient having to come back for a second visit and without requiring the dentist to purchase expensive in-office milling equipment.

FIG. 1 is a cutaway view illustrating a prepared tooth with a sleeve-crown pair installed thereon in accordance with exemplary embodiments of the present disclosure. As can be seen from this figure, an at least partially translucent sleeve 20 is bonded to the properly prepared tooth 50 using light-curing cement 40, in the manner described herein. The crown 10 is then glued to the sleeve 20 using an adhesive or cement compound 30 thereby giving the patient a permanent crown in a single sitting.

While the figures and their associated description discuss the fitting of the aforementioned sleeve-crown pair to a prepared tooth 50 that remains attached to a natural tooth root 60, it is to be understood that the sleeve-crown pair may be similarly installed onto an abutment of a dental implant that has been installed into the jaw bone of the patient.

Figure 2:
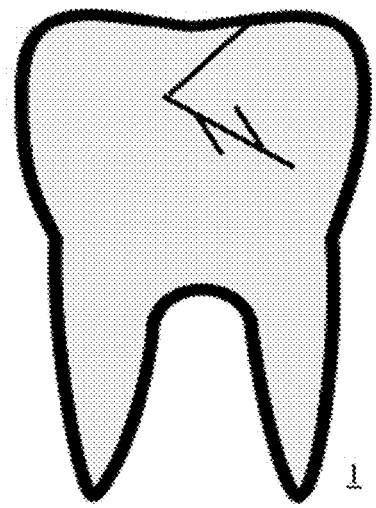
FIG. 2 is a representation of a diseased or damaged tooth.

FIG. 2 is a representation of a diseased or damaged tooth 1 that has not yet been prepared. The damaged tooth 1 may be damaged as a result of tooth decay, physical trauma, or structural break down of a natural tooth or a previously applied restoration that may occur over time with normal use. Where this damage cannot be effectively repaired by fillings, inlays, or onlays, a dental crown may be used according to a dentist's preferred course of treatment.

Figure 8:
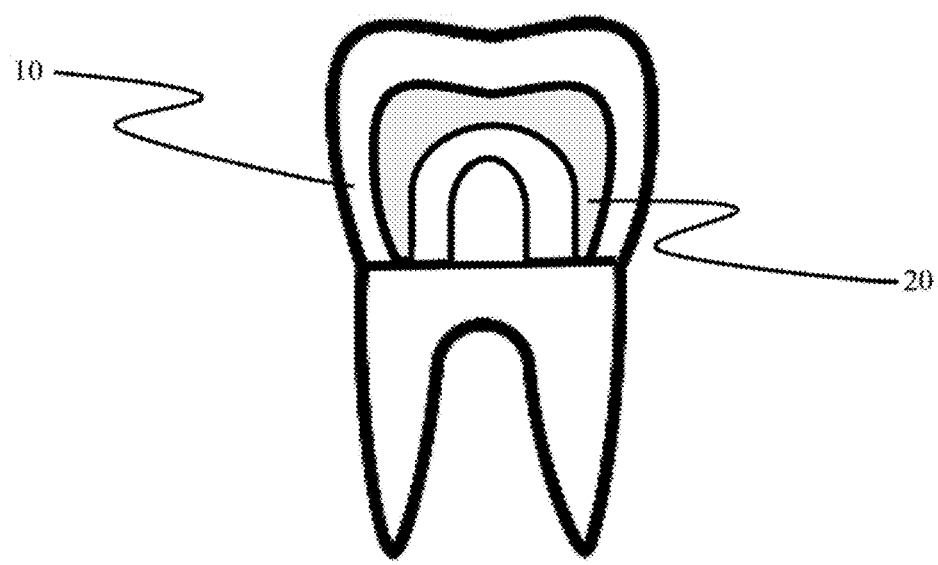
FIG. 8 is a cutaway view illustrating a crown adhered to a cemented sleeve in accordance with exemplary embodiments of the present disclosure.
Figure 9:
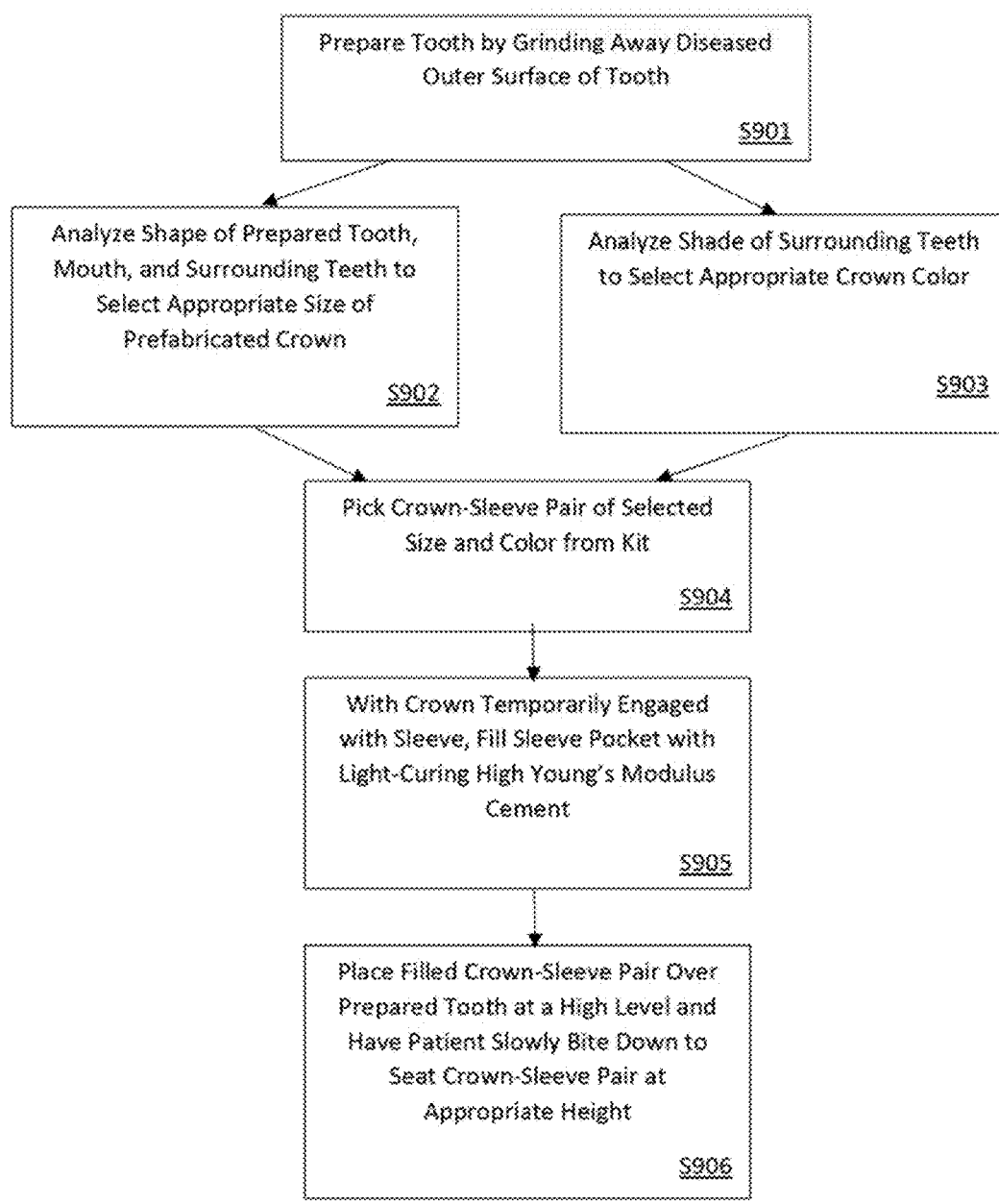
FIGS. 9 and 10 are flow charts illustrating a method for performing a dental crown restoration in accordance with exemplary embodiments of the present disclosure.
Figure 10:
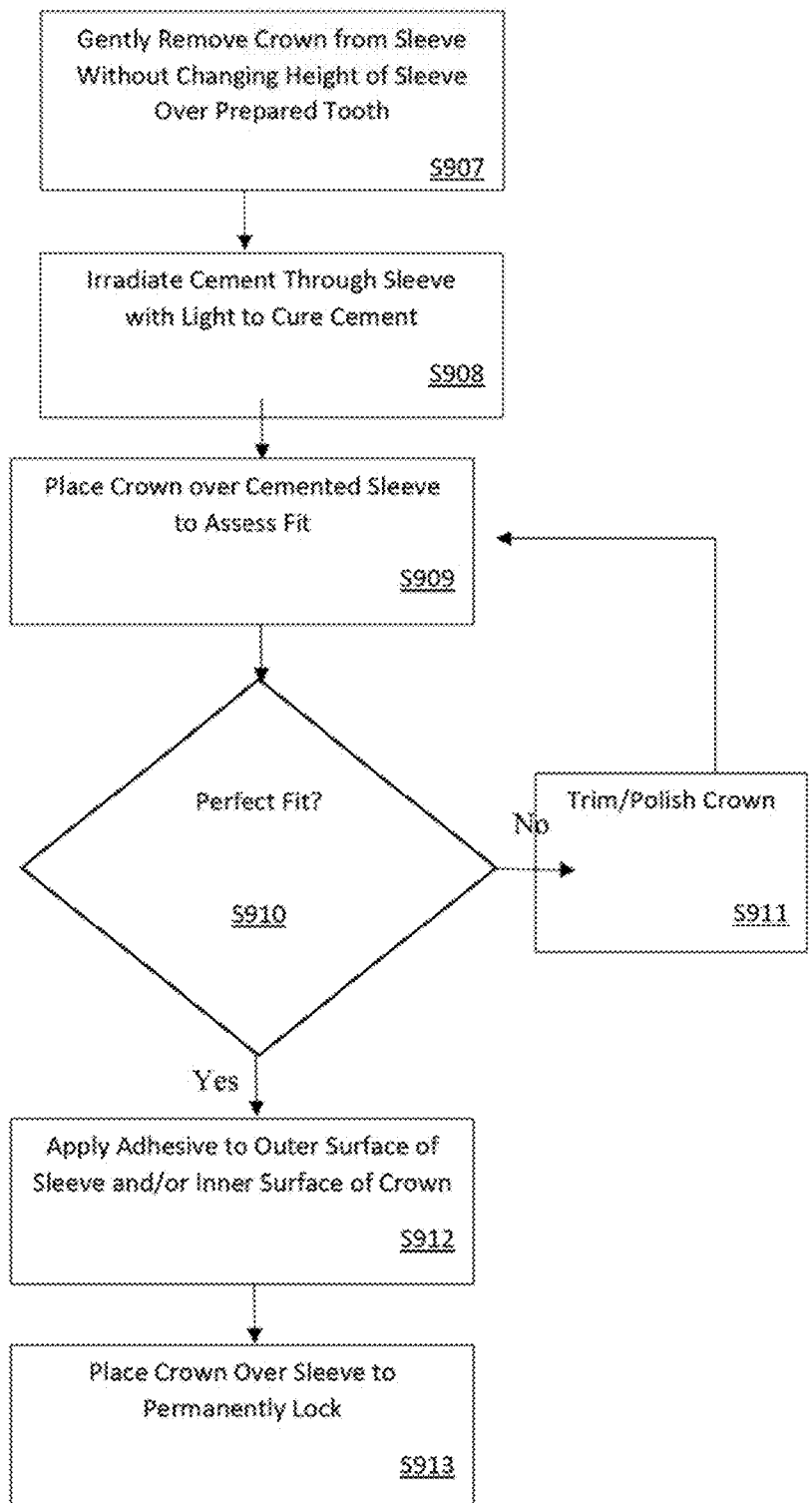

FIGS. 9 and 10 are flow charts illustrating a method for performing a dental crown restoration in accordance with exemplary embodiments of the present disclosure. The structures illustrated in FIGS. 2-8 will now be explained in connection with the method represented in FIGS. 9 and 10.

Figure 3:
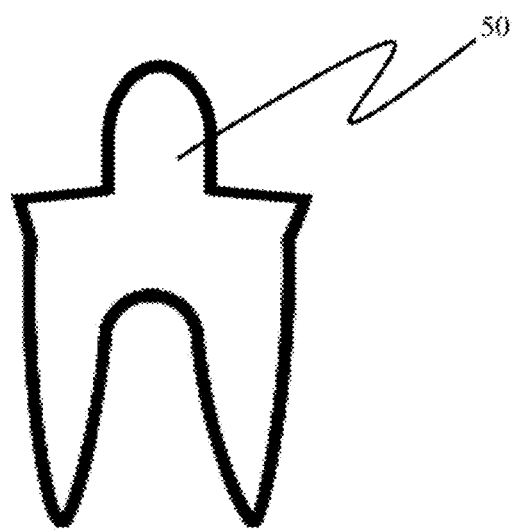
FIG. 3 is a cross-sectional view of a prepared tooth in accordance with exemplary embodiments of the present disclosure.

Exemplary embodiments of the present invention may begin with the preparation of the damaged tooth 1. FIG. 3 is a cross-sectional view of a prepared tooth 50 in accordance with exemplary embodiments of the present disclosure. As can be seen from this figure, the prepared tooth 50 may be prepared by grinding the outer surface of the tooth to achieve a prepared tooth having a post-shape (Step S901). The size and shape of the prepared tooth may depend largely on the extent of the damage to the tooth as the prepared tooth must be free of damage. In accordance with exemplary embodiments of the present disclosure, the dentist may use judgement to prepare the tooth to a post of a desired size and shape.

After preparation has been completed, the shape of the prepared tooth, mouth, and surrounding teeth may be analyzed to select an appropriate size of prefabricated crown (Step S902) and the color of the surrounding teeth may be analyzed to select an appropriate crown color (Step S903).

Selecting the appropriate size for the crown may include scanning the prepared tooth and surrounding mesial-distal area with a digital scanner. A computer may then be used to determine the optimal crown size to use such that the selected crown will fit well between the neighboring teeth and engage well with the bite of the opposite tooth. The digital scanner and computer may also be used to assess tooth color and select an appropriate crown color.

Rather than use digital sizing, a mechanical dental caliper or printed sizing gauge tool may be used to measure the optimal size of the crown to be used and a printed color chart may be used to select a desired color. However, it is to be understood that some amount of trimming and/or polishing may be performed at a later point to allow the selected crown to better fit between neighboring teeth, where necessary. It is also to be understood that the exact height at which the sleeve-crown pair fits upon the prepared tooth may be adjusted in the manner described below and so there is some degree of customization that can be performed on the selected prefabricated tooth to allow for a smaller number of crown sizes to choose between.

There may be any number of differently sized prefabricated crowns to choose from and there may be a different selection of crown sizes that depend on the type of tooth being repaired. For example, there may be some number of sizes of prefabricated crowns for molars, some number of sizes of prefabricated crowns for premolars, some number of sizes of prefabricated crowns for canines, and some number of prefabricated crowns for incisors. While it is contemplated that exemplary embodiments of the present invention may be used to crown any tooth, the crowning of molars is primarily described herein for the purpose of providing a simplified disclosure. According to one exemplary embodiment, there may be five differently sized crowns to fit each of the molars of most adults.

The crowns of each size may be made available in one of a number of different shades. The number of different shades that may be prefabricated and included as part of a dental restoration kit may depend on the type of tooth being crowned as the closeness of a color match for incisors may be easier to detect than the closeness of a color match for molars. Thus, a kit of prefabricated crowns and sleeves that would include incisors and molars may include more color shade options for incisors than for molars. Some kits may be limited to prefabricated crown and sleeve pairs for just molars, other kits may include prefabricated crown and sleeve pairs for all teeth, including incisors, canines, premolars, and molars, or any combination thereof. According to one exemplary embodiment, there may be three differently colored crowns to crown the molars of most adults.

Accordingly, the kit of prefabricated molar crowns may include crowns of five different sizes, each with three different shades, for a total of fifteen different crowns for restoring one tooth.

In the dental restoration kit, each crown may be coupled to a matching sleeve and so the optimal selection of crown size and color may be made and picked from the dental restoration kit along with its matched sleeve (Step S904). However, in the dental restoration kit, each crown need not be pre-matched with a proper sleeve and in that case, a kit guide may be used to select an appropriate sleeve size for the desired crown.

Figure 4:
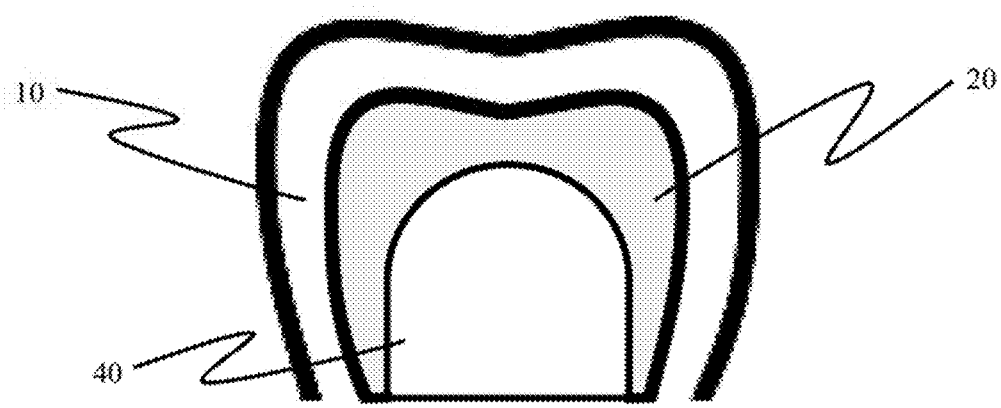
FIG. 4 is a cutaway view illustrating a sleeve-crown pair in accordance with exemplary embodiments of the present disclosure.

FIG. 4 is a cutaway view illustrating a sleeve-crown pair in accordance with exemplary embodiments of the present disclosure. As can be seen from this figure, the selected crown 10 and its associated at least partially translucent sleeve 20 may be temporarily engaged with each other, which is to say, the crown 10 may be placed over the sleeve 20 without adhesives. The crown 10 and sleeve 20 pair may then be placed over the prepared tooth 50 to provide a preliminary test fit. If the crown 10 is too wide to fit between neighboring teeth, the crown 10 may be trimmed and/or polished a bit to allow for the preliminary test fitting. If the preliminary test fitting reveals that the incorrect crown size had been selected or the incorrect color had been selected, then the selection of the optimal sleeve-crown pair may need to be redone at this time.

Once the preliminary test fitting has been successfully performed, the inner cavity of the sleeve 20, which may be referred to herein as the sleeve pocket 40, may be filled with a light-curing cement having a high Young's modulus (Step S905). This cement may include a composite resin such as a glass ionomer. The cement may have the same Young's modulus as the crown 10 and sleeve 20.

Figure 19:
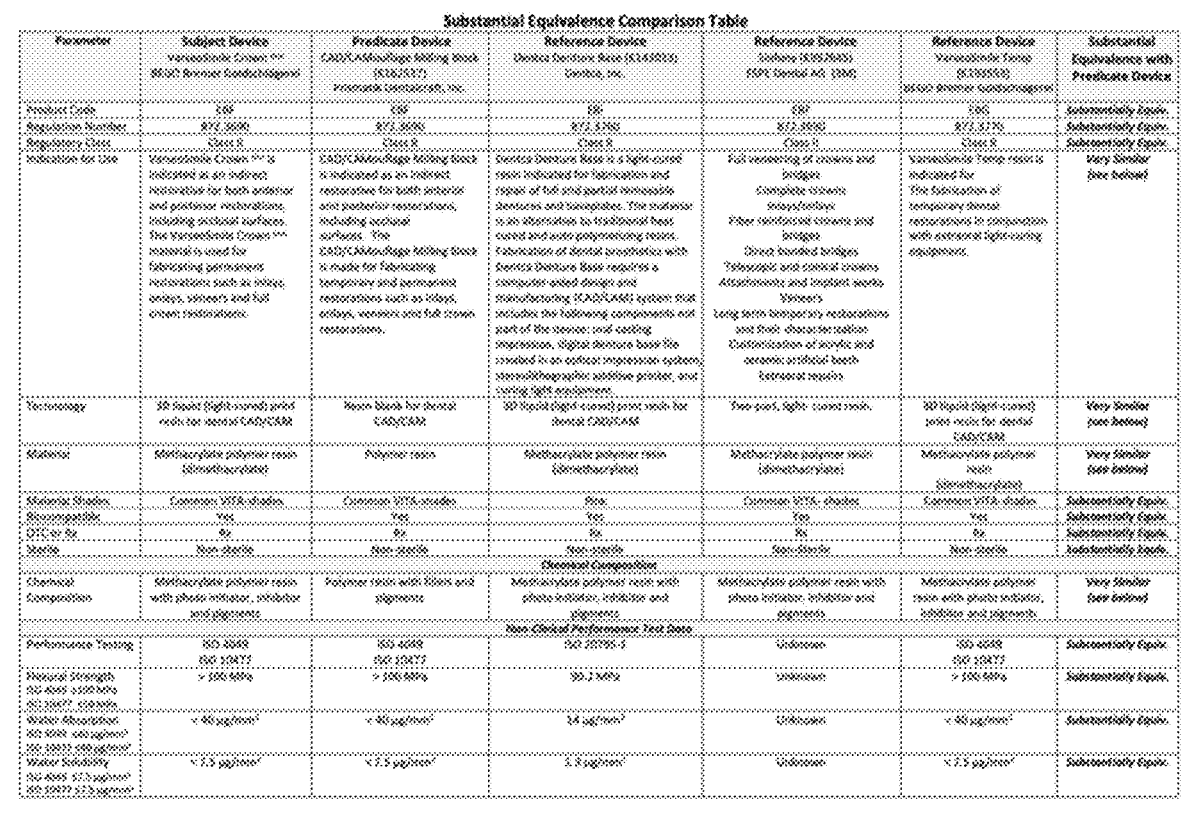

It is noted that the crown 10 may be made of a base material such as a polymer with ceramic particles dispersed therein. Traditionally, crowns may be made of partially stabilized zirconia (zirconium dioxide $ZrO_2$+Yttrium Oxide $Y_2O_3$) or porcelain fused to metal (PFM) which provide for a strong crown having a realistic tooth-like appearance. However, to better allow for trimming/polishing, exemplary embodiments of the present invention may construct the prefabricated crowns 10 using a polymer base, which may facilitate trimming/polishing and may also allow for fabrication by injection-molding or printing, which would not be practical for zirconia or porcelain crowns. The polymer base may be impregnated with ceramic particles and/or glass particles, or strong nanomaterials, to provide the crown with an enduring hardness that is resistant to chipping and cracking. For example, the particles of ceramic and/or glass may comprise 40-85% of the total volume of the impregnated polymer. Any polymer may be used for this purpose. FIGS. 17-19 are tables illustrating examples of materials that may be used in the dental crowns in accordance with exemplary embodiments of the present disclosure.

FIG. 17 is a table illustrating examples of materials that may be used to form the crowns 10 and/or sleeves 20 in accordance with exemplary embodiments of the present disclosure. Shown are the material names, the concentration of fillers and polymers that may be used, by weight, and the name of an exemplary manufacturer.

FIG. 18 is a table illustrating examples of materials that may be used to form the crowns 10 and/or sleeves 20 in accordance with exemplary embodiments of the present disclosure. Shown are the material names, measured hardness, measured elastic modulus, and measured composition by weight percent. To the extent that the measured composition differs from the compositions provided in FIG. 17, it is noted that FIG. 17 shows idealized values while FIG. 18 shows measured values.

FIG. 19 is a table illustrating examples of materials that may be used to form the crowns 10 and/or sleeves 20 in accordance with exemplary embodiments of the present disclosure. Shown are the material names, a brief description of how these materials may be used, and other pertinent technical details.

For example, the sleeve 20 may include the same or different materials from the crown 10. For example, the crown and sleeve may each include Bego Varseo (which can be 3D printed), HR smart blocks (hybrid ceramic) (injection moldable), Camouflage from Glidewell (injection moldable), GC initial LRF block (leucite reinforced glass ceramic) (machinable), tetric CAD (hybrid ceramic resin) (machinable), and/or Shofu block HC (hybrid ceramic) (machinable). Each of these aforementioned materials may be considered a polymer.

The crown 10 may have an exterior surface that is smooth and made to look like a natural tooth having a natural pattern of cusps, grooves, and pits on the occlusal surface. The interior surface of the crown 10 may substantially match the exterior surface of the crown so as to provide a nearly constant thickness throughout the crown 10, although it is to be understood that the interior surface of the crown 10 does not necessarily have the same level of detail as the exterior surface of the crown 10. According to some exemplary embodiments of the present disclosure, the crown 10 may have a nearly constant thickness throughout all side surfaces, with a somewhat larger thickness at the occlusal surface. However, it is to be understood that the thickness of the crown 10 along the side surfaces may tapper towards the gumline.

By conforming the contours of the inner surface of the crown 10 to the contours of the outer surface of the crown 10, the crown 10 may achieve maximum structural strength while allowing for a large cavity within its inner surface.

The shape of the exterior surface of the sleeve 20 may precisely match the shape of the interior surface of the crown 10, in an inverted manner, so that the two elements may precisely engage and mate together. Thus, the exterior surface of the sleeve 20 may have a similar shape to the exterior surface of the crown 10, which may be a substantially anatomical shape of the occlusal surface of the crown 10.

Alternatively, the interior surface of the crown 10 may be domed and the exterior surface of the sleeve 20 may be inversely domed. However, this arrangement might not distribute biting force as well as the above-described approach, might create a weaker bond between crown and sleeve, and might make for a thicker crown 10 at its sides and thereby reduce the ability of the sleeve 20 to accommodate thicker prepared tooth posts. Thus, by conforming the shape of the outer surface of the sleeve 20 to that of the outer surface of the crown 10, the sleeve 20 may be made to accommodate a wider range of prepared tooth sizes.

The interior surface of the crown 10 and the exterior surface of the sleeve 20 may alternatively be shaped with any manner of structures to increase coupling between crown 10 and sleeve 20, however, as described above, the conformal shape design may allow for the accommodation of a wider range of prepared tooth sizes.

It is further noted that the interior surface of the crown 10 may be made rough and the exterior surface of the sleeve 20 may be made similarly rough so as to better allow for the bonding of these surfaces to an adhesive that is applied between these two surfaces, as is described in greater detail bellow. This roughness may be equivalent to an RA of 40-150. However, more generally, this roughness may be equivalent to an RA of 12-350.

The sleeve 20 may be constructed of a material that is at least partially translucent to light of a wavelength that is used to cure dental cement such as that described in greater detail below. The sleeve 20 may have substantially the same composition as the crown 10. This will allow the two elements to better bond together without separation over time. Where different materials are used for the sleeve 20 and the crown 10, they should have the same stiffness, for example, the same Young's modulus.

For example, the sleeve 20 may be constructed of a polymer. The sleeve 20, like the crown 10, may be made by injection molding and so a polymer is well suited for this means of fabrication. However, the sleeve 20 may alternatively be made by printing, casting, or milling and so the sleeve may be constructed of other materials that are at least partially translucent in the desired wavelength. According to an exemplary embodiment of the present disclosure, the sleeve 20 may be made of the same material as the crown 10.

The sleeve 20 may be non-porous so as to prevent the dental cement from penetrating its interior surface and the sleeve 20 may be rigid so as to maintain its fixed shape.

The interior surface of the sleeve 20 may also be conformal to its exterior surface so as to permit the sleeve 20 to be thinner while keeping a desired structural strength. In this case, the interior surface of the sleeve 20 would also have the aforementioned anatomic shape. Alternatively, the interior surface of the sleeve 20 may be shaped as a simple dome or cylinder with a domed top 624.

It is noted that the interior pocket of the sleeve 20 should be relatively large. This may allow for the sleeve 20 to be relatively thin so as to enhance translucency thereof. Also, the relatively large interior pocket of the sleeve 20 may allow for the accommodation of a larger prepared tooth post 50, as it is not known at the time of fabrication how large the prepared tooth post 50 will be. However, a majority of the internal volume 40 of the sleeve 20 may be filled with the cement, after the restoration is complete. For example, the prepared tooth may occupy 20% to 50% of the volume of the internal volume 40 of the sleeve 20, with the cement occupying the remaining 80% to 50%. However, this is not necessarily the case, and the prepared tooth 50 may occupy a majority of the internal volume 40 of the sleeve 20, for example, between 50% and 80% thereof, with the cement occupying the remaining 50% to 20% of the internal volume 40 of the sleeve 20. However, as is described below, the internal cavity 40 of the sleeve 20 may be fully filled with the cement prior to applying the sleeve 20 to the prepared tooth 50.

The sleeve pocket 40 is filled with a dental cement (Step S905). The dental cement used should be light-curing and should have a high Young's modulus so as to be sufficiently rigid to allow for proper chewing on the crown 10, even when the volume of the sleeve pocket 40 is relatively large. The dental cement, once light-cured, may occupy a substantial volume of the complete dental restoration and so for this reason, it needs to be sufficiently rigid.

Accordingly, the crown 10, the sleeve 20, and the cement should have a high Young's modulus within a range of 2 and 60 GPa. Moreover, the Young's modulus of the crown 10, the sleeve 20, and the cement should substantially match each other. For example, the Young's modulus of the sleeve 20 should be within +/−0.3% of that of the crown 10. The Young's modulus of the cement should be within 1% to 35% of that of the sleeve 20, as the matching between the Young's modulus of the cement to the sleeve 20 is less critical than that of the sleeve 20 to the crown 10.

As discussed above, the crown 10 may be shaded with one of a selection of particular colors. The coloration of the crown 10 may block light. Even though both the sleeve 20 and the crown 10 may be made of the same material, the sleeve 20 may be more translucent to light than crown 10 because it is thinner and also because it is not shaded.

Exemplary embodiments of the present disclosure may provide premade crowns 10 of one of a number of different shades. There are 16 shades within Vita Pan Classical Shade Guide and so exemplary embodiments of the present disclosure may have as many as 16 differently shaded crowns 10. However, this many shades might not be necessary as 3 different shades may be used to match with up to 85% of the population, with molar crowns 10 requiring fewer shades than other teeth as it may be harder to perceive shading in such teeth.

Examples of suitable dental cements having a high Young's modulus may include GC FujiCEM. Suitable dental cements may be light-curing, such as infra-red or ultraviolet light curing. The dental cement may include a silane additive, which may be used to increase polymer bond. The dental cement may be a glass ionomer material that may include one or more of, for example, silica ($SiO_2$), alumina ($Al_2O_3$), aluminum fluoride ($AlF_3$), calcium fluoride ($CaF_2$), sodium fluoride (NaF), aluminum phosphate ($AlPO_4$), barium oxide, strontium oxide, polyacrylic acid, a copolymer of acrylic acid, other carboxylic acids (e.g., itaconic acid or maleic acid), and/or tartaric acid.

Figure 5:
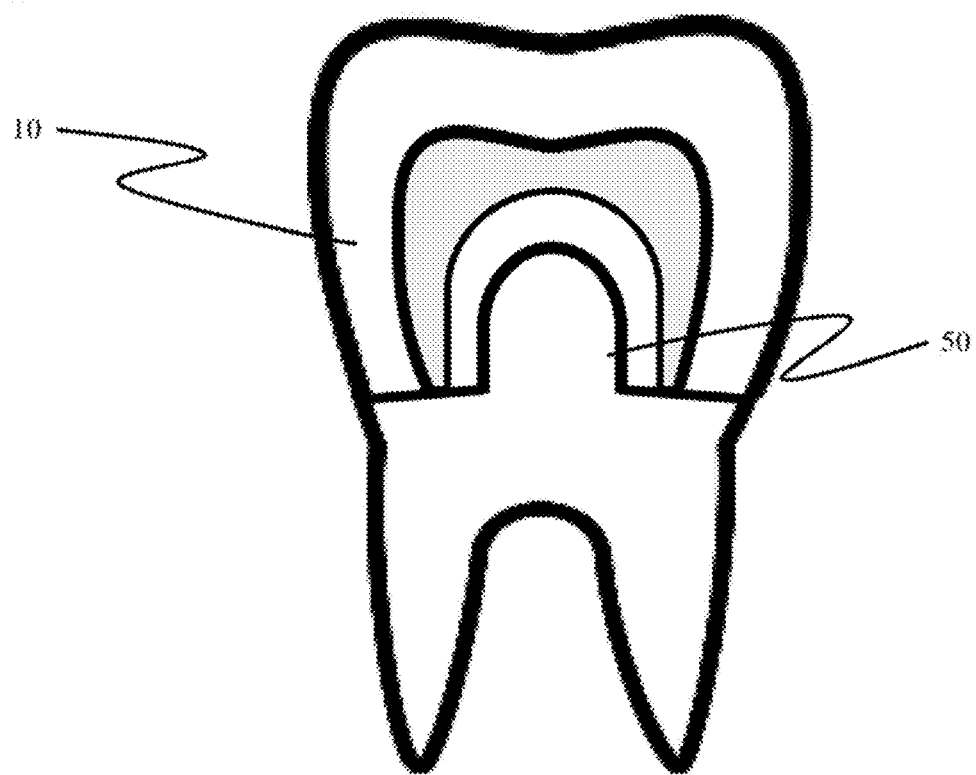
FIG. 5 is a cutaway view illustrating a sleeve-crown pair temporarily placed on a prepared tooth in accordance with exemplary embodiments of the present disclosure.

FIG. 5 is a cutaway view illustrating a sleeve-crown pair temporarily placed on a prepared tooth 50 in accordance with exemplary embodiments of the present disclosure. With the crown 10 still disposed over the sleeve 20, without the use of adhesives therebetween, and the sleeve pocket filled with the light-curing high Young's modulus cement, the dental restoration is placed over the prepared tooth 50 (Step S905). However, at this stage, the dental restoration is placed at a relatively high level above the plane of the gum line. The patient is then asked to slowly bite or tap down thereby pushing the dental restoration into its ideal height, relative to the gum line (Step S906). Any runoff of uncured cement may be cleaned away at this time.

Continuing on to the process shown in FIG. 10, the crown 10 is then gently removed from the sleeve 20 such that the sleeve 20 maintains its ideal distance from the gum line (Step S907). This exposes the exterior surface of the sleeve.

Figure 6:
FIG. 6 is a cutaway view illustrating the light-curing of cement through a sleeve fitted to a prepared tooth in accordance with exemplary embodiments of the present disclosure.

FIG. 6 is a cutaway view illustrating the light-curing of cement through a sleeve 20 fitted to a prepared tooth 50 in accordance with exemplary embodiments of the present disclosure. As seen in this figure, a light source 70 is then used to light cure the dental cement within the interior volume 40 of the sleeve 20 through the at least partially translucent sleeve 20 (Step S908) while the crown 10 has been removed. For example, an infrared light source may be used to cure the dental cement, which is an infrared-curing material. Alternatively, the light source 70 may be an ultraviolet light source and the dental cement may include an ultraviolet-cured material. In either case, because the sleeve 20 is relatively thin and at least partially translucent to the spectrum of light produced by the light source 70, the dental cement within the interior volume 40 may be effectively cured so as to form the aforementioned dominant volume of the dental restoration.

Next, the fit of the crown 10 over the sleeve 20 may be fully tested. This may include placing the crown 10 back over the sleeve 20, without the use of an adhesive therebetween (Step S909). If the fit is perfect (Yes, S910) then the method may proceed to the permanent adhesion of the crown 10 to sleeve 20. However, if there is insufficient space between the sides of the crown 10 and the sides of the neighboring teeth (insufficient mesial/distal spacing) (No, Step S910) then the crown 10 may be trimmed and/or polished (Step S911). The process of performing the test fitting and trimming/polishing may be repeated until the perfect fit is achieved (Yes, S910).

Figure 7:
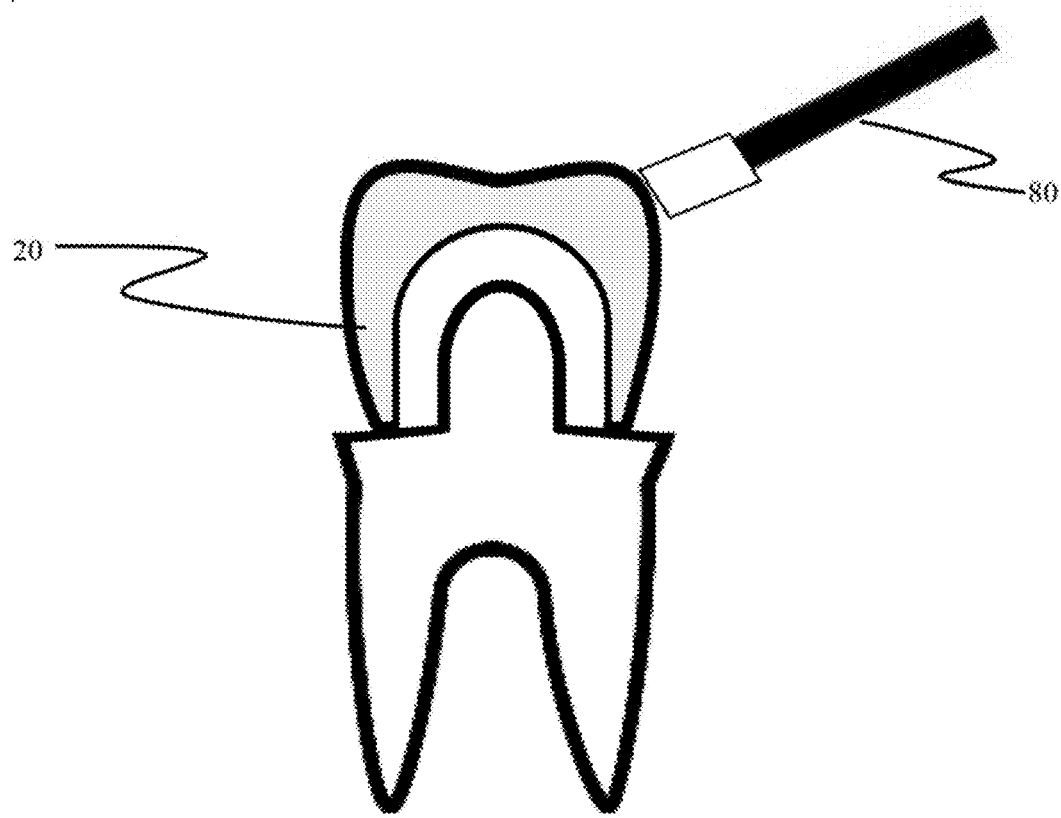
FIG. 7 is a cutaway view illustrating the application of an adhesive to an outer surface of a cemented sleeve in accordance with exemplary embodiments of the present disclosure.

FIG. 7 is a cutaway view illustrating the application of an adhesive to an outer surface of a cemented sleeve 20 in accordance with exemplary embodiments of the present disclosure. As can be seen from this figure, the crown 10 may be once again removed from the sleeve 20 and the exterior surface of the sleeve 20 may be covered with an adhesive (Step S912), for example, suing a brush 80 or other application device. The adhesive may also be, or may alternatively be, applied to the interior surface of the crown 10 and then the crown 10 may be placed over the sleeve 20 so as to permanently lock the crown 10 to the sleeve 20 (Step S913). The adhesive used may be any of a wide range of suitable dental adhesive or dental cement used for dental restorations such as lute glass or 3M Relyx Unicem dental cement or adhesive.

FIG. 8 is a cutaway view illustrating a crown 10 adhered to a cemented sleeve 20 in accordance with exemplary embodiments of the present disclosure. As can be seen from this figure, the dental restoration is complete.

It is noted that there might be no elements disposed between the crown 10 and sleeve 20 other than the aforementioned adhesive and the interior surface of the crown 10 and the exterior surface of the sleeve 20 may be so shaped for precise mating. Thus, according to exemplary embodiments of the present disclosure, no structure of plastic or metal, whether rigid or mesh, is disposed between crown 10 and sleeve 20, other than a thin layer of adhesive. It is further noted that the thin layer of adhesive is applied to the interior surface of the crown 10 and/or the exterior surface of the sleeve 20 in a substantially liquid or gelatinous form so as to conform to the shapes and structures of the crown 10 and sleeve 20 and so this adhesive is not applied as a rigid and/or solid mass.

Additionally, in accordance with exemplary embodiments of the present disclosure, the sleeve 20 itself, as described above, is substantially rigid and is formed of a contiguous and homogeneous material. Thus, the sleeve 20 is not a fabric, mesh, chain-link, etc. For example, the sleeve 20 may be non-porous and, as described above, may be made of a same material as the crown 10. The sleeve 20 may therefore be at least partially translucent to the frequency of light used to cure the cement contained in its inner volume 40 by virtue of light being able to pass through the material of its composition, rather than by being able to pass through holes or pores thereof. However, alternatively, the sleeve 20 may be opaque in which case the dental cement may be cured by another means such as time curing or by the conduction of heat through the sleeve 20 by a heating element.

It is further noted that the sleeve 20 is disposed between the crown 10 and the prepared tooth 50 and, according to exemplary embodiments of the present disclosure, the sleeve 20 is not intended and is not suitable for use as a crown 10 itself. For example, the sleeve 20 is not polished to be smooth as a natural tooth would be and the sleeve 20 is not tinted to match the color of the patient's surrounding tooth. It is further noted that the sleeve 20 need not have an anatomical look of a tooth and may instead have any suitable shape, such as a substantially cylindrical structure with a flat or domed top. It is only the crown 10 that is polished and tinted so as to appear as a natural tooth. This arrangement allows for the cement within the interior volume 40 of the sleeve 20 to be more easily cured using light, such as infrared light, as it is understood that polishing the surface of the sleeve 20 and/or tinting the surface of the sleeve 20 could make transmission of curing light therethrough more difficult.

Moreover, by utilizing the sleeve 20 and crown 10 combination in which the crown 10 may be trimmed to fit between surrounding teeth, no trimming or polishing of the sleeve 20 may be needed. However, according to some exemplary embodiments of the present disclosure, the sleeve 20 may be trimmed or polished to provide a better fit, particularly (although not necessarily) in the interior of the sleeve 20 so as to better accommodate the prepared tooth 50. Moreover, the exterior surface of the sleeve 20 may also be trimmed, along with the crown 10, to better accommodate the mesial-distal spacing between the neighboring teeth.

Figure 11:
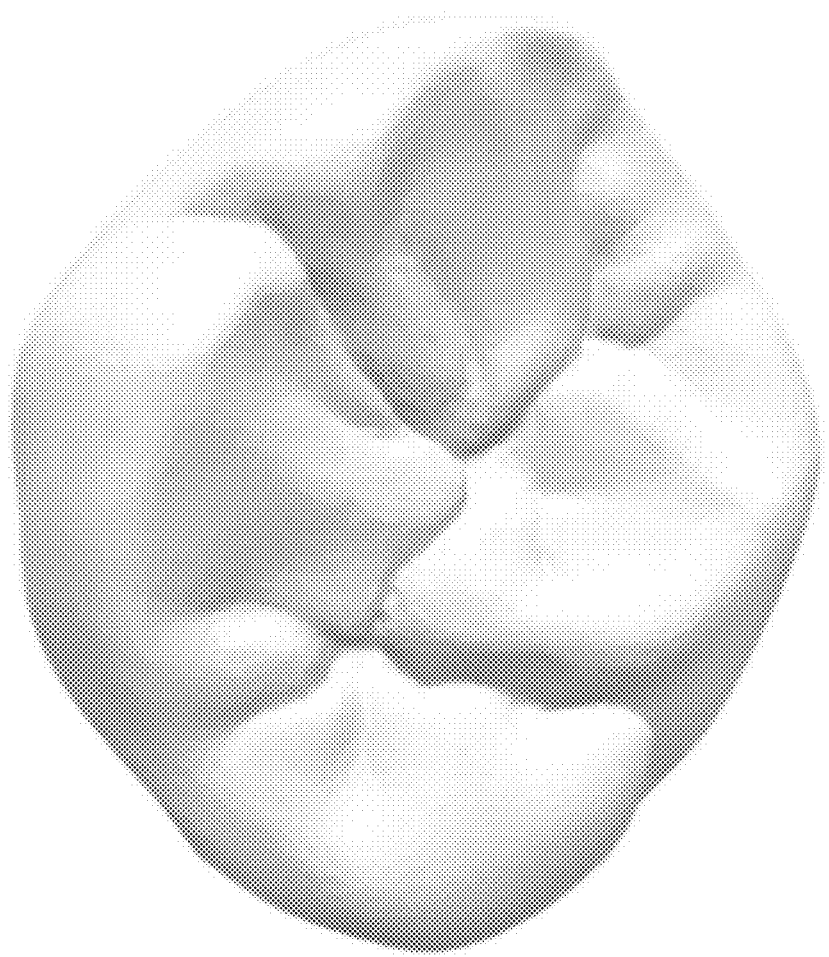
FIGS. 11-13 are perspective views illustrating a molar crown in accordance with exemplary embodiments of the present disclosure.
Figure 12:
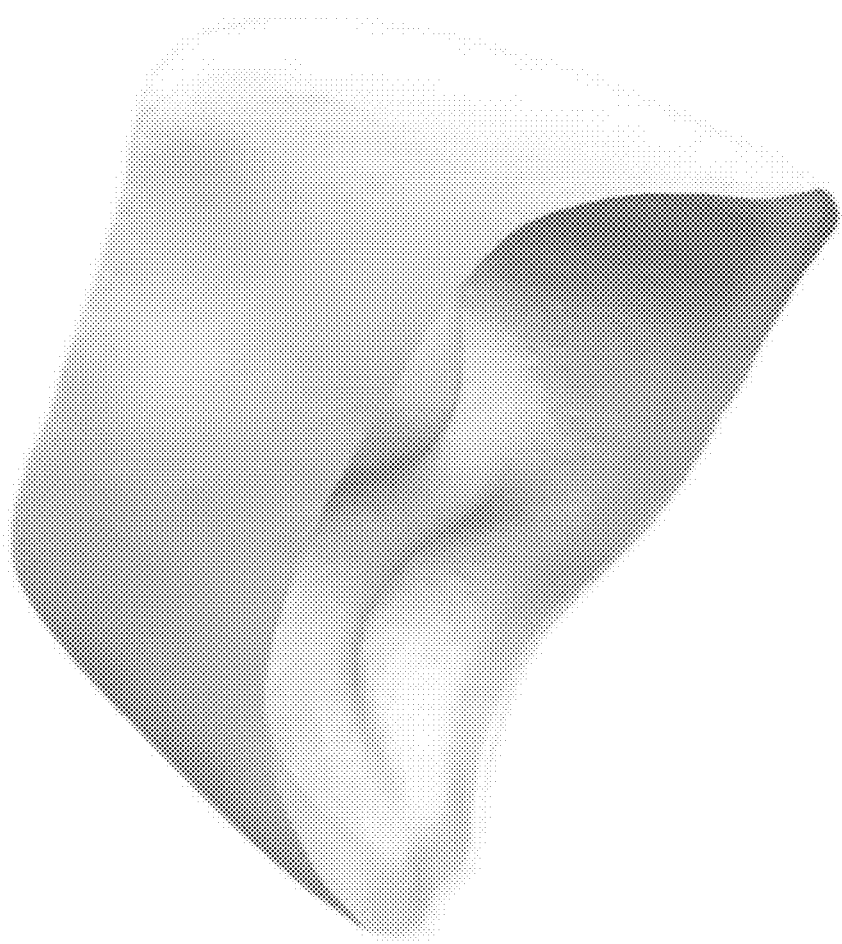
Figure 13:
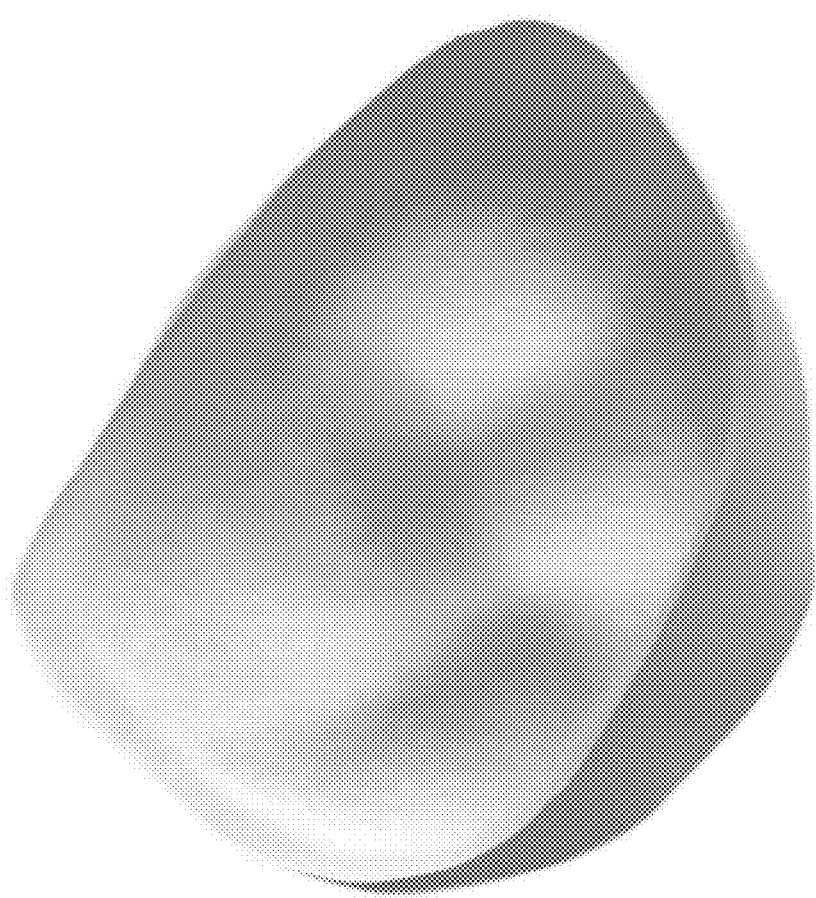

FIGS. 11-13 are perspective views illustrating a molar crown in accordance with exemplary embodiments of the present disclosure. For the purposes of describing these figures, the occlusal surface of the crown 10 is called the top surface (although it should be understood that the terms top and bottom are only used for the convenience of description and the dental restoration may be oriented in any direction). FIG. 11 shows a perspective view of the top surface of the crown 10, here shown as a crown used for a molar restoration. The anatomical top shape of the crown 10, including its occlusal surface, can be appreciated from this figure. FIG. 12 shows a first side view of the molar crown 10 shown in FIG. 11. Here it can be appreciated that the interior surface has an inverse-anatomical shape. The exterior sides are shown as being smooth and finished while the interior surface is shown as being rough. FIG. 13 shows a bottom surface of the molar crown 10 shown in FIG. 11. Here it can be appreciated that the interior surface has an inverse-anatomical shape and a rough surface texture. The relative thinness of the crown 10 may also be appreciated from this figure. The thickness of the crown 10 may be between 0.3 mm at the sides to 2.5 mm at the occlusal surface.

Figure 14:
FIGS. 14-16 are perspective views illustrating a molar sleeve in accordance with exemplary embodiments of the present disclosure.
Figure 15:
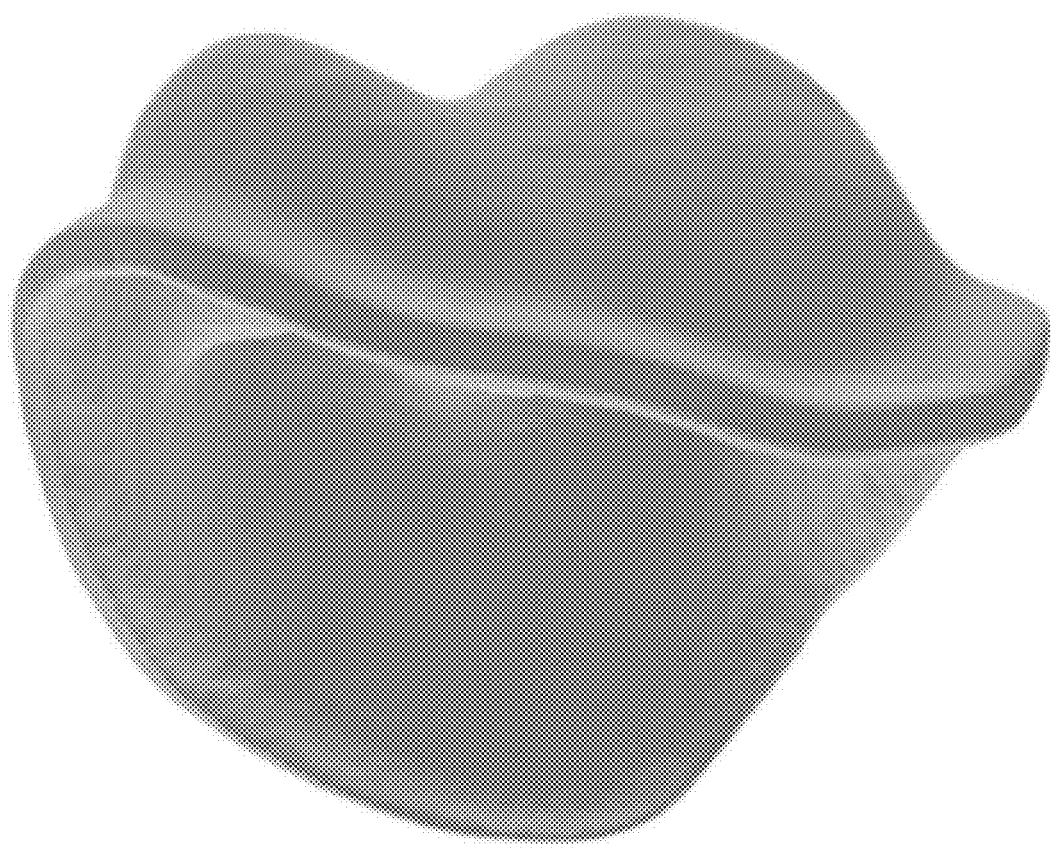
Figure 16:
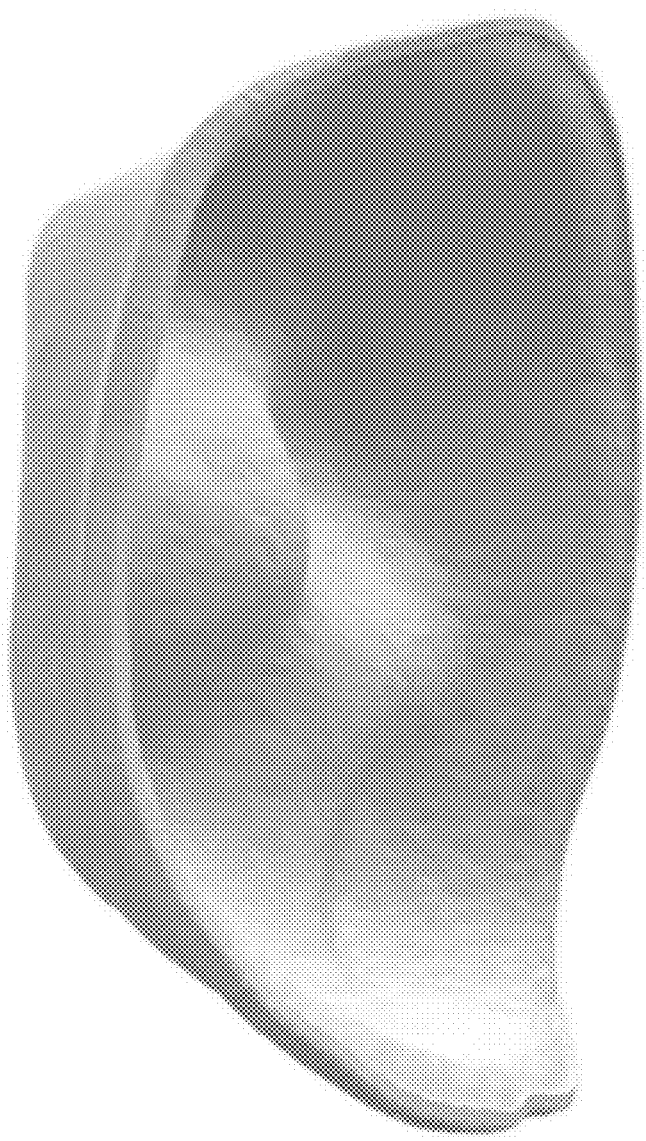

FIGS. 14-16 are perspective views illustrating a molar sleeve 20 in accordance with exemplary embodiments of the present disclosure. For the purpose of describing these figures, the crown-facing surface is referred to herein as the top while the gum-facing surface is referred to herein as the bottom. FIG. 14 shows a perspective side view of the sleeve 20. It can be appreciated that the top/exterior surface of the sleeve 20 has the anatomical shape and there is a flange surrounding the bottom of the sleeve 20. The flange, which has a shape similar to the brim of a hat, is an optional feature and may be used to receive the bottom of the crown 10. It can also be appreciated from this figure that the top/exterior surface of the sleeve has a rough texture. FIG. 15 shows a perspective side view of the sleeve 20 shown in FIG. 14. As can be appreciated from this figure, just as the top/exterior surface has the anatomical shape, the bottom/interior surface has an inverse-anatomical shape and that both of these surfaces have a rough texture. As can be seen from this figure, the flange has a thickness that is equal to that of the remainder of the sleeve 20. FIG. 16 shows a perspective bottom view of the sleeve 20 shown in FIG. 14. As can be appreciated from this figure, the bottom/interior surface has an inverse-anatomical shape and a rough texture. The relative thinness of the sleeve 20 may also be appreciated from this figure. The sleeve 20 may be between 0.3 mm to 1.5 mm thick.

Digital Guidance

Exemplary embodiments of the present disclosure relate to a method for creating digital guidance in the preparation of a tooth to be used in conjunction with prefabricated crowns and related bushings and sleeves. According to this approach, intraoral images of the patient's mouth may be taken prior to preparing the affected tooth. The intraoral images may include a visual image of the exterior surfaces of the patient's dental arch as well as x-rays of the interior structure of the dental arch. These intraoral images are then digitally processed to generate a three-dimensional model of the patient's dental arch in which both interior and exterior visualizations are merged. The affected tooth is then either automatically identified or selected by the dental clinician. Computer vision is then used to segment an area of disease within the affected tooth within the merged model. A desired volume of removal is then automatically identified from within the merged model based on removing the area of disease from the affected tooth and then creating a desired shape from the remaining healthy tooth, the desired shape being suitable to interface with a prefabricated bushing/sleeve and a prefabricated crown. Tooth preparation guidance is then created so as to delineate the volume of removal from the desired shape. The preparation guidance is then overlaid with a surface image of the patient's dental arch in accordance with one of a number of visualization modalities that are described in detail herein. The dental clinician may then utilize the digital guidance visualization in the preparation of the affected tooth. Thereafter, the prepared tooth may be fitted with a bushing/sleeve and a prefabricated tooth may be installed over the bushing/sleeve.

Figure 20:
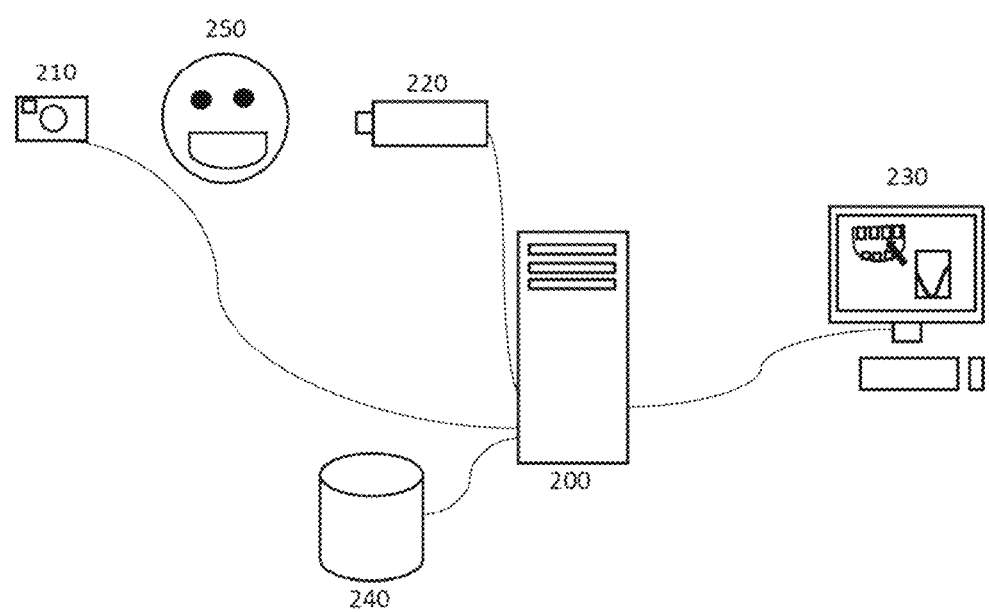
FIG. 20 is a schematic diagram illustrating a system for creating digital guidance in the preparation of a tooth to be used in conjunction with prefabricated crowns and related bushings/sleeves in accordance with exemplary embodiments of the present invention.
Figure 21:
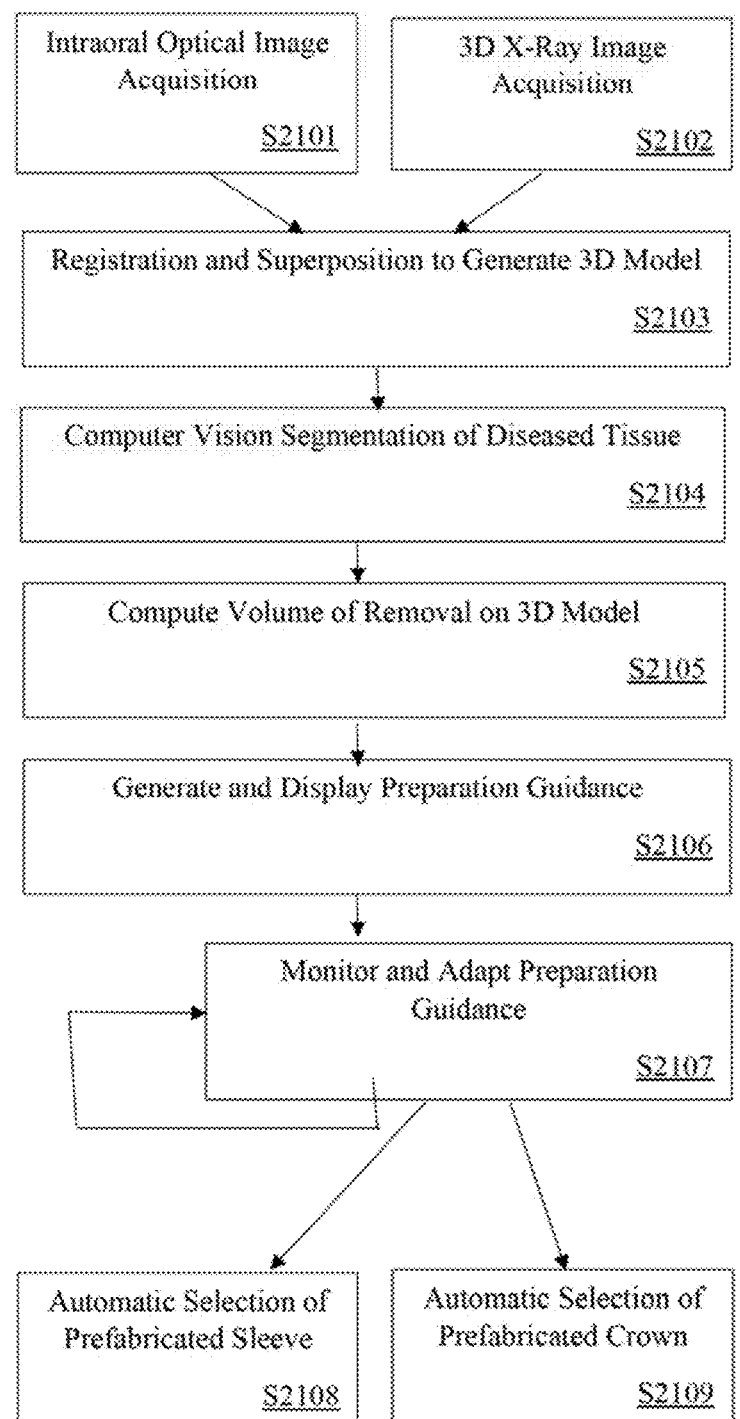
FIG. 21 is a flowchart illustrating a method for creating digital guidance in the preparation of a tooth to be used in conjunction with prefabricated crowns and related bushings/sleeves in accordance with exemplary embodiments of the present invention.

FIG. 20 is a schematic diagram illustrating a system for creating digital guidance in the preparation of a tooth to be used in conjunction with prefabricated crowns and related bushings/sleeves and FIG. 21 is a flowchart illustrating a method for creating digital guidance in the preparation of a tooth to be used in conjunction with prefabricated crowns and related bushings/sleeves, in accordance with exemplary embodiments of the present invention.

The patient 250 may have one or more affected teeth. An affected tooth is one in which there is disease or damage, such as decay or other structural impairments, that require dental restoration. Before the affected tooth is prepared, an optical imager 210, such as a digital camera, etc., may be used to acquire an intraoral optical image of the patient's entire dental arch, or some portion thereof (Step S2101). The acquired image may be a 3D image that is taken either with a stereographic imager or an imager with a single lens may be used to acquire intraoral images from multiple different angles. An x-ray imager 220, or some other imaging modality able to acquire structural/internal images of the patient's teeth, may be used to acquire structural/internal images of the entire dental arch, or some portion thereof (Step S2102). For the purpose of providing a simplified description, this imaging modality that acquires structural/internal images of the teeth will be referred to herein as an x-ray imager 220, although it is to be understood that other modalities may be used such as a sonogram, MRI, etc. This x-ray imager 220 may also be a 3D imager or it may be used to acquire x-ray images from multiple angles so as to generate a 3D image at a later step.

The acquired images (both optical and x-ray) may be sent to an image processing server 200. The image processing server 200 may either be local to the dental office, or remote and accessible over a wide area network (WAN) such as the Internet, and thus may be embodied as a cloud-based service. The image processing server 200 may perform image registration so as to generate a 3D model that identifies each individual tooth of the dental arch, and the bounds and limits thereof (Step S2103). Image registration may be performed volumetrically for both the optical images and the x-ray images and then the two sets of images may be combined into a single 3D model that includes optical data for the surfaces of the teeth as well as x-ray data for the interior and structural elements of the teeth.

The image processing server 200 may thereafter perform computer vision segmentation on the teeth so as to label each voxel of the 3D model as either disease or healthy (Step S2104). This determination may either automatic or assisted. Where it is assisted, a clinician may use a guidance console 230 to label one or more points of the 3D model as seed points for diseased tissue and then a region growing algorithm, for example, may be used to identify all other voxels that are part of the region of disease. The clinician may be shown the segmentation on the guidance console 230 and may use the guidance console 230 to adjust or accept the segmentation results. The guidance console 230 may be a computer terminal or another means for digital input/output and the clinician may also use the guidance console 230 to show a desired portion of the 3D model and/or the optical images and x-rays so as to verify that the segmentation results accurately reflect the bounds of the diseased tissue.

The image processing server 200 may thereafter define a removal volume on the 3D model (Step S2105). The removal volume may be an area which the clinician is to remove from the tooth. The removal volume therefore includes an entirety of the diseased tissue plus some predetermined margin of healthy tissue and such additional healthy tissue as is needed to be removed so as to be left with a shape of a prepared tooth that is suited for fitting within one of a plurality of sleeve sizes.

The sleeve and/or bushing (referred to herein as "sleeve") is an adaptive element configured to receive the prepared tooth at one end thereof (a "tooth-wise end") and to receive the prefabricated crown at an opposite end thereof (a "crown-wise end"). The clinician may be in possession of a set or kit of sleeves that have a combination of different sizes at the tooth-wise end and different sizes at the crown-wise end. There may be a finite set of different sizes at each of the crown-wise end and the tooth-wise end. The shape of the tooth-wise end may be a substantially cylindrical cavity with a radius and height. For example, there may be 4 different radiuses and 4 different heights to the cylindrical cavity of the tooth-wise end. In this case there need not be 16 different possible combinations of radius and height as smaller radiuses may only be associated with smaller heights and larger radiuses may be associated with larger heights, but there will be some number of possible sizes for the tooth-wise end, for example, there may be 8 different sizes.

Similarly, the crown-wise end of the sleeve may have a peg shape configured to mate with a plurality of differently sized and shaped prefabricated crowns. According to some exemplary embodiments of the present disclosure, there need only be one such size of peg for the crown-wise end of the sleeve. However, there may alternatively be several differently sized pegs with larger peg shapes being used for larger crowns and smaller peg shapes being used with smaller crowns. Thus, there may be 3 different peg shapes for the crown-wise end of the sleeve. Thus, there may be 24 different sleeves in the kit representing every possible combination of tooth-wise ends and crown-wise ends, although these numbers are merely offered as an example, and there may be any number of shapes or sleeves used.

The dimensions of the available sleeves are recorded in a selection database 240 that is accessible by the image processing server 200 and so these dimensions may be used by the image processing server 200 in computing the removal volume so that after the removal volume is removed from the affected tooth, the affected tooth has a perfect shape to receive one of the sleeves, which has been selected according to some criteria, such as the largest possible radius that allows for the complete removal of the diseased tissue plus the aforementioned margin.

Figure 22:
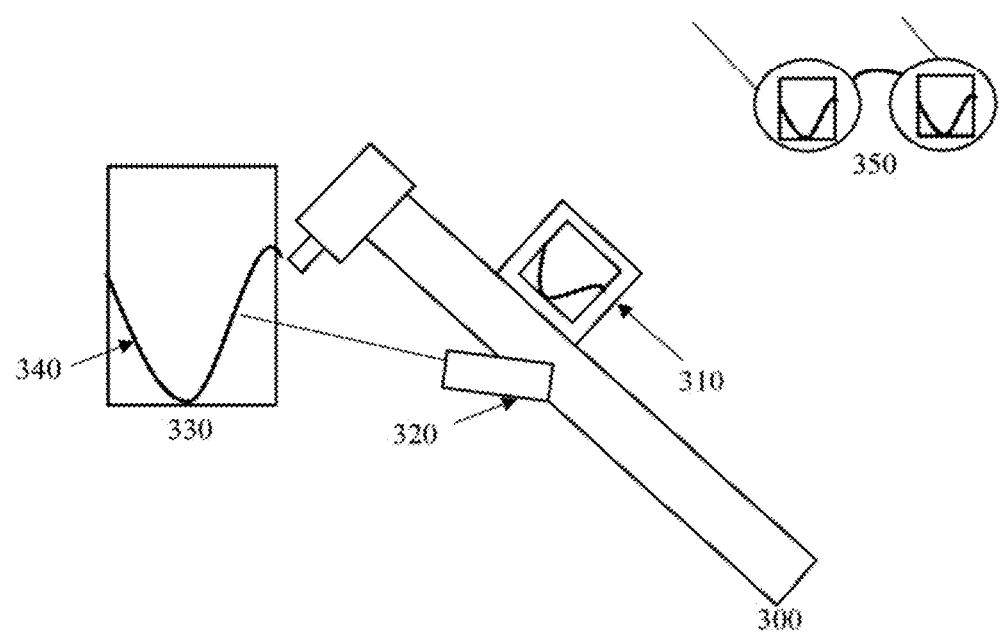
FIG. 22 is a schematic diagram illustrating some of the possible forms in which preparation guidance may be displayed in accordance with exemplary embodiments of the present invention.

The image processing server 200 may thereafter compute, from the removal volume, preparation guidance (Step S2106). Preparation guidance is an indication of the delineation between the removal volume and what is to remain of the affected tooth so as to mate with the tooth-wise end of the sleeve so as to serve as guidance for the clinician to know what portions of the tooth are to be removed. The preparation guidance may be displayed in one or more different forms. FIG. 22 is a schematic diagram illustrating some of the possible forms in which preparation guidance may be displayed.

In a simplest form, the preparation guidance may be displayed on the guidance console 230. In this example, the clinician may see from the display on the guidance console 230 what must be removed from the tooth, and as this guidance may be updated as the clinician drills, the clinician may look back and forth between the guidance console 230 and the tooth to ensure accurate drilling.

Alternatively, the preparation guidance may be displayed on a small display 310 that has been mounted on the dental drill 300. This small display 310 may include a display unit, an attachment means for attaching the small display 310 to the dental drill 300, an image processing unit, such as a system-on-chip (and other related components), a battery for supplying power, and a wireless adapter for receiving the preparation guidance wirelessly, from the image processing server. The small display 310 may alternatively receive preparation guidance from a wire connection that runs parallel to the power connection of the dental drill 300. By mounting this display 310 to the dental drill 300, the clinician need not have to look away from the tooth to see the preparation guidance.

Alternatively, a guidance projector 320 may be incorporated into the dental drill 300. This element may be embodied as a laser-diose laser pointer that is mechanically actuated and/or includes a lens/mirror element that is mechanically actuated or otherwise controlled by electrical signal. The laser-diode laser pointer 320 may project cut lines 340 using one or more laser points that are scanned across the tooth surface 330. Alternatively, the guidance projector 320 may use a backlight, an LCD imager, and lenses to project a display of the projected guidance 340 onto the affected tooth 330.

According to another approach, the guidance may be displayed using augmented reality glasses 350 worn by the dental clinician so that the guidance may be highlighted in 3D over the actual tooth, as seen by the dental clinician, for example, as coloration or some iconic indicator.

As mentioned above, the preparation guidance may be updated in real-time as the clinician drills. This may be accomplished, for example, by the continuous use of the optical imager 210 to determine a current image of the affected tooth, which may be used to update the 3D model and thus the guidance (Step S2107). As it may be difficult to obtain a clear view of the teeth during the drilling, an optical imager 210 may be incorporated into the drill 300 and/or accelerometers may be used in the drill 300 to keep track of its movements so as to help infer what has been removed from the tooth in real-time.

This monitoring and adaptation of the preparation guidance may continue until the desired shape of the prepared tooth is obtained. However, should the clinician determine that further drilling is required to clear the diseased tissue, the preparation guidance may adapt to additional drilling beyond the preparation guidance by defining a new removal volume that leaves a smaller prepared tooth and perhaps fits a smaller-sized tooth-wise end of a sleeve.

After the tooth has been fully prepared, the optical imager may be used to ensure the desired tooth preparation has been achieved and then the image processing server may select a desired prefabricated crown (Step S2109) so as to best match the size and shape of the dental arch and mouth of the patient and may select a desired sleeve (Step S2108) so as to have the desired tooth-wise end to match the prepared tooth and to have the desired crown-wise end to match the selected crown. The guidance console may show the clinician which crown and sleeve have been selected. Thereafter, the clinician may cement the sleeve to the prepared tooth and the crown to the sleeve so as to implement the restoration.

Figure 23:
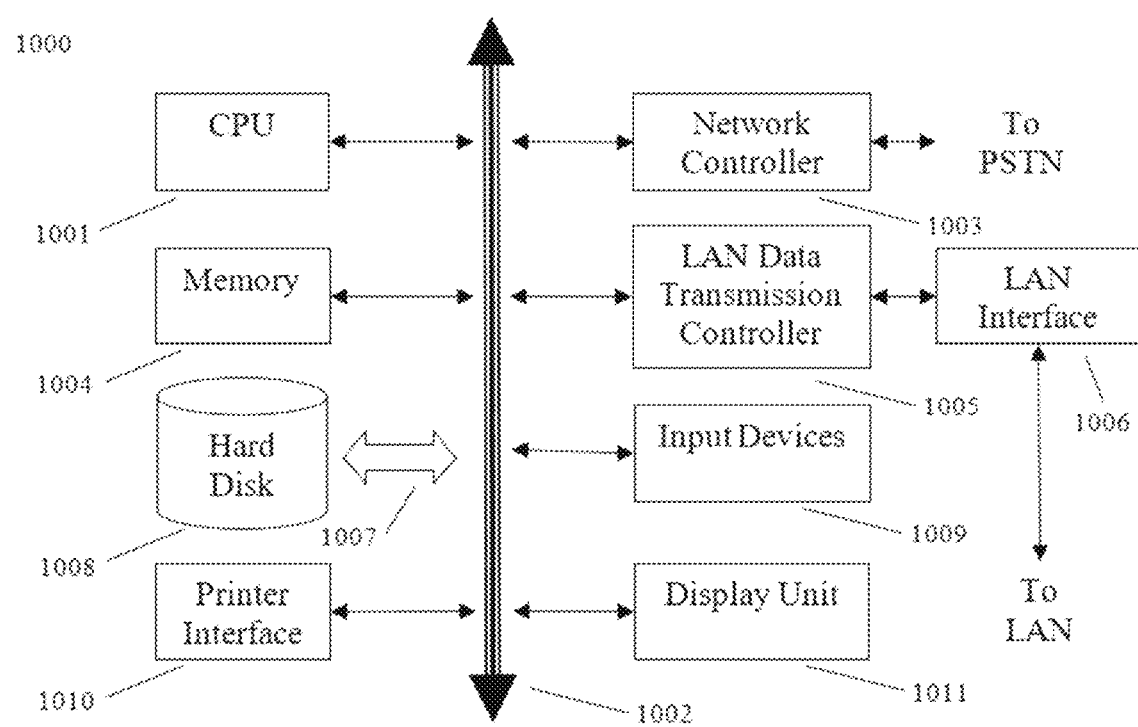
FIG. 23 shows an example of a computer system capable of implementing the method and apparatus according to embodiments of the present disclosure.

FIG. 23 shows an example of a computer system which may implement a method and system of the present disclosure. The image processing server and/or the guidance console may be implemented as such a computer system. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 1000 may include, for example, a central processing unit (CPU) 1001, random access memory (RAM) 1004, a printer interface 1010, a display unit 1011, a local area network (LAN) data transmission controller 1005, a LAN interface 1006, a network controller 1003, an internal bus 1002, and one or more input devices 1009, for example, a keyboard, mouse etc. As shown, the system 1000 may be connected to a data storage device, for example, a hard disk, 1008 via a link 1007.

Haptic Guidance

Exemplary embodiments of the present disclosure relate to a method for providing haptic guidance in the preparation of a tooth to be used in conjunction with prefabricated crowns and related bushings and sleeves. According to this approach, intraoral images of the patient's mouth may be taken prior to preparing the affected tooth. The intraoral images may include a visual image of the exterior surfaces of the patient's dental arch as well as x-rays of the interior structure of the dental arch. These intraoral images are then digitally processed to generate a three-dimensional model of the patient's dental arch in which both interior and exterior visualizations are merged. The affected tooth is then either automatically identified or selected by the dental clinician. Computer vision is then used to segment an area of disease or other structural defect within the affected tooth within the merged model. A desired volume of removal is then automatically identified from within the merged model based on removing the area of disease from the affected tooth and then creating a desired shape from the remaining healthy tooth, the desired shape being suitable to interface with a prefabricated bushing/sleeve and a prefabricated crow. Tooth preparation guidance is then created so as to delineate the volume of removal from the desired shape. The preparation guidance is then displayed to the clinician. The dental clinician may then utilize the digital guidance display in the preparation of the affected tooth, for example, by drilling away the volume of removal using a dental drill that incorporates a haptic sleeve. Intraoral images are captured as the drilling is performed and these images are registered to the 3D model to compare the present location of the drill to the volume of removal. When the drill is determined to come into contact with a boundary between the volume of removal and the volume of tooth to be preserved, haptic feedback is provided by haptic sleeve so that the clinician may be made aware of having reached the boundary. This may continue until the preparation of the tooth has been completed.

Thereafter, the prepared tooth may be fitted with a bushing/sleeve and a prefabricated tooth may be installed over the bushing/sleeve.

Figure 24:
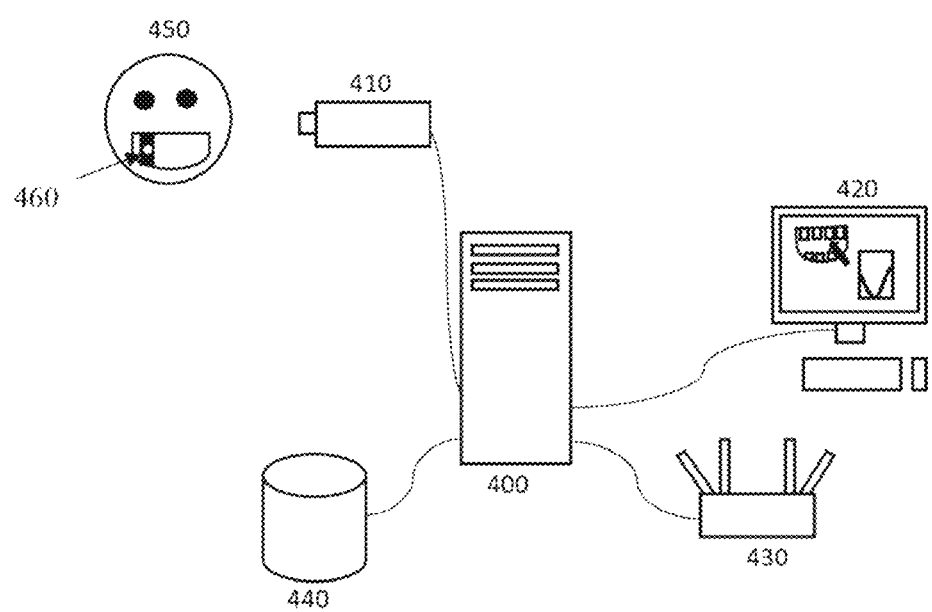
FIG. 24 is a schematic diagram illustrating a system for providing haptic guidance in the preparation of a tooth to be used in conjunction with prefabricated crowns and related bushings/sleeves in accordance with exemplary embodiments of the present invention.
Figure 25:
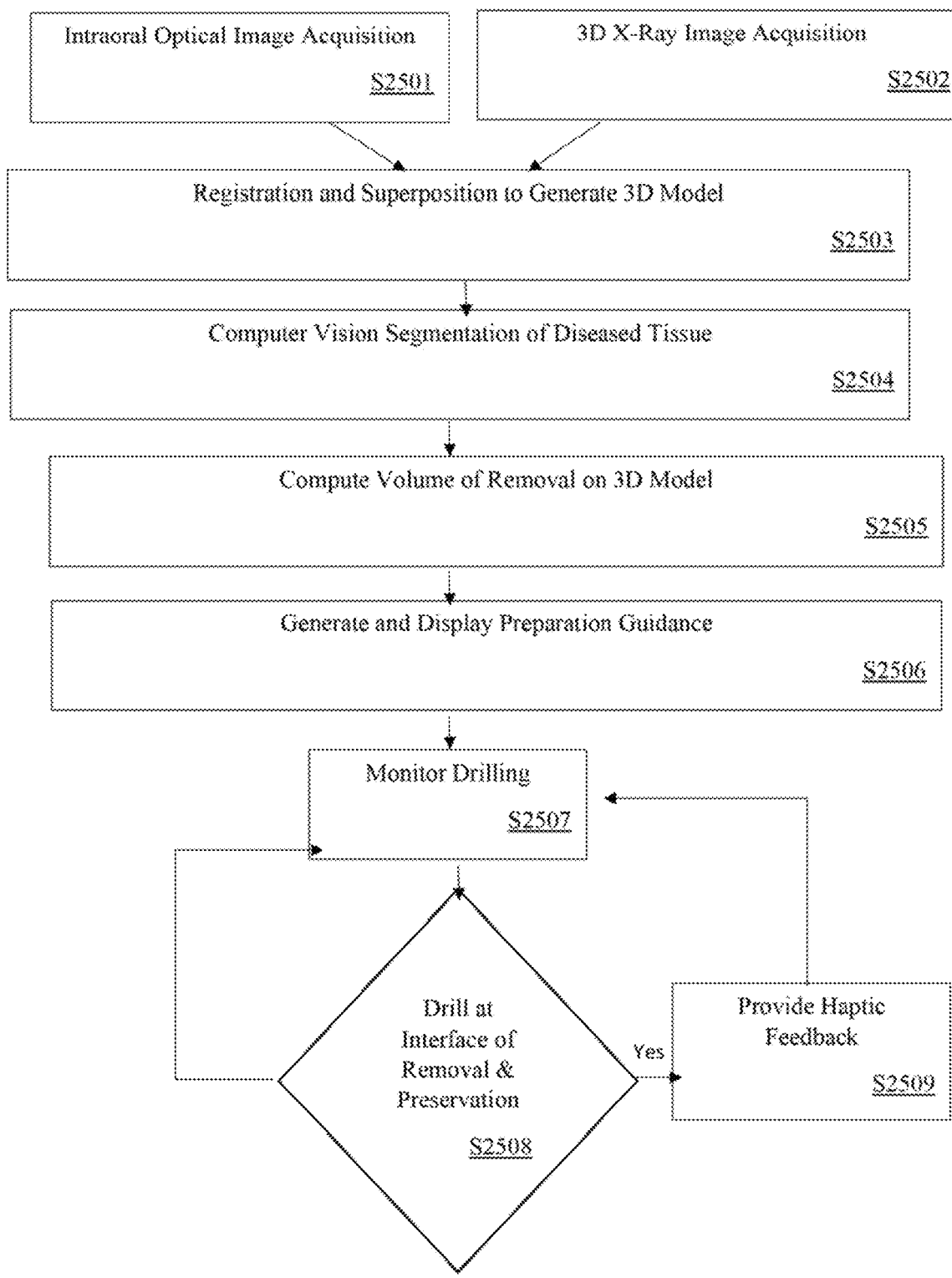
FIG. 25 is a flowchart illustrating a method for providing haptic guidance in the preparation of a tooth to be used in conjunction with prefabricated crowns and related bushings/sleeves in accordance with exemplary embodiments of the present invention.

FIG. 24 is a schematic diagram illustrating a system for providing haptic guidance in the preparation of a tooth to be used in conjunction with prefabricated crowns and related bushings/sleeves and FIG. 25 is a flowchart illustrating for providing haptic guidance in the preparation of a tooth to be used in conjunction with prefabricated crowns and related bushings/sleeves, in accordance with exemplary embodiments of the present invention.

The patient 450 may have one or more affected teeth. An affected tooth is one in which disease, such as decay or other structural impairments, that require dental restoration. A jaw immobilizer device 460 may be inserted into the patients mouth so as to hold the jaw in an open position. The jaw immobilizer 460 may include a bite block and an optical imager, such as a small video camera, disposed therein. The optical imager may be configured to capture images of the patient's 450 teeth from within the patient's mouth and the jaw immobilizer 460 may further include other elements that may help acquire imagery such as a flash.

The jaw immobilizer 460 may further include electronic hardware for operating the optical imager and transmitting optical imagery acquired therefrom to an image processing server. Such hardware may include a battery for supplying power to the optical imager and a wireless transmitter for transmitting the imagery wirelessly to the image processing server, for example, via a wireless access point 430 connected thereto. The jaw immobilizer 460 may further include docking pins for allowing the battery to be recharged when the jaw immobilizer 460 is docked between use. The optical imager and related hardware may be encased within the jaw immobilizer 460 within a shielding box for protecting the electronics disposed therein from liquid/heat/UV light, etc. that the jaw immobilizer 460 may be exposed to between uses for the purpose of providing sterilization thereto. Alternatively, the optical imager may be connected to an image processing server 400 via a tether which provides power to the optical imager and transmits data from the optical imager to the image processing server 400.

Before perpetration of the affected tooth begins, the optical imager may be used to acquire an intraoral optical image of a portion of the patient's 450 dental arch that includes the affected tooth (Step S2501). The optical imager may include two lenses for acquiring stereographic images. An x-ray imager 410, or some other imaging modality able to acquire structural/internal images of the patient's 450 teeth, may be used to acquire structural/internal images of the patient's dental arch (Step S2502). For the purpose of providing a simplified description, this imaging modality that acquires structural/internal images of the teeth will be referred to herein as an x-ray imager 410, although it is to be understood that other modalities may be used. This x-ray imager 410 may also be a 3D imager or it may be used to acquire x-ray images from multiple angles so as to generate a 3D image at a later step.

The acquired images (both optical and x-ray) may be sent to the image processing server 400. The image processing server 400 may either be local to the dental office, or remote and accessible over a wide area network (WAN) such as the Internet, and thus may be embodied as a cloud-based service. The image processing server 400 may perform image registration so as to identify each individual tooth of the dental arch, and the bounds and limits thereof (Step S2503). Image registration may be performed volumetrically for both the optical images and the x-ray images and then the two sets of images may be combined into a single 3D model that includes optical data for the surfaces of the teeth as well as x-ray data for the interior and structural elements of the teeth.

The image processing server 400 may thereafter perform computer vision segmentation on the teeth so as to label each voxel of the 3D model as either disease or healthy (Step S2504). This determination may either automatic or assisted. Where it is assisted, a clinician may use a guidance console 420 to label one or more points of the 3D model as seed points for diseased tissue and then a region growing algorithm, for example, may be used to identify all other voxels that are part of the region of disease. The clinician may be shown the segmentation on the guidance console 420 and may use the guidance console to adjust or accept the segmentation results. The guidance console 420 may be a computer terminal or another means for digital input/output and the clinician may also use the guidance console 420 to show a desired portion of the 3D model and/or the optical images and x-rays so as to verify that the segmentation results accurately reflect the bounds of the diseased tissue.

The image processing server 400 may thereafter define a removal volume on the 3D model (Step S2505). The removal volume may be an area which the clinician is to remove from the tooth. The removal volume therefore includes an entirety of the diseased tissue plus some predetermined margin of healthy tissue and such additional healthy tissue as is needed to be removed so as to be left with a shape of a prepared tooth that is suited for fitting within one of a plurality of sleeve sizes.

The volume of the tooth that is not part of the removal volume may be considered the preservation volume of the tooth.

The sleeve and/or bushing (referred to herein as "sleeve") is an adaptive element configured to receive the prepared tooth at one end thereof (a "tooth-wise end") and to receive the prefabricated crown at an opposite end thereof (a "crown-wise end"). The clinician may be in possession of a set or kit of sleeves that have a combination of different sizes at the tooth-wise end and different sizes at the crown-wise end. There may be a finite set of different sizes at each of the crown-wise end and the tooth-wise end. The shape of the tooth-wise end may be a substantially cylindrical cavity with a radius and height. For example, there may be 4 different radiuses and 4 different heights to the cylindrical cavity of the tooth-wise end. In this case there need not be 16 different possible combinations of radius and height as smaller radiuses may only be associated with smaller heights and larger radiuses may be associated with larger heights, but there will be some number of possible sizes for the tooth-wise end, for example, there may be 8 different sizes.

Similarly, the crown-wise end of the sleeve may have a peg shape configured to mate with a plurality of differently sized and shaped prefabricated crowns. According to some exemplary embodiments of the present disclosure, there need only be one such size of peg for the crown-wise end of the sleeve. However, there may alternatively be several differently sized pegs with larger peg shapes being used for larger crowns and smaller peg shapes being used with smaller crowns. Thus, there may be 3 different peg shapes for the crown-wise end of the sleeve. Thus, there may be 24 different sleeves in the kit representing every possible combination of tooth-wise ends and crown-wise ends, although these numbers are merely offered as an example, and there may be any number of shapes or sleeves used.

The dimensions of the available sleeves are recorded in a selection database 440 that is accessible by the image processing server 400 and so these dimensions may be used by the image processing server 400 in computing the removal volume so that after the removal volume is removed from the affected tooth, the affected tooth has a perfect shape to receive one of the sleeves, which has been selected according to some criteria, such as the largest possible radius that allows for the complete removal of the diseased tissue plus the aforementioned margin.

The image processing server 400 may thereafter compute, from the removal volume, preparation guidance and the preparation guidance may thereafter be displayed (Step S2506). Preparation guidance is an indication of the delineation between the removal volume and the preservation volume of the affected tooth so as to mate with the tooth-wise end of the sleeve so as to serve as guidance for the clinician to know what portions of the tooth are to be removed. The preparation guidance may be displayed on the guidance console 420.

The optical imager may continuously acquire optical imagery as the clinician drills at the affected tooth so that the drilling may be monitored (Step S2507). The optical imagery may be continuously sent to the image processing server 400 and the 3D model may be updated accordingly. As the optical imager may acquire imagery of the drill as it enters the patient's 450 mouth, the image processing server 400 may monitor the position of the drill with respect to the removal volume within the 3D model. When it is determined, based on the monitored position of the drill within the 3D model, that the drill is within a designated distance from an interface between the removal volume and the preservation volume (Yes, Step S2508), the image processing server may transmit to the haptic sleeve an activation signal and the haptic sleeve may provide haptic feedback in response to the received activation signal (Step S2509). The haptic feedback may be a vibration, which is to say, a rapid back-and-forth motion, or the haptic feedback may be a kick sensation such as the drill being pushed in a direction away from the affected tooth. In either case, the image processing server may be used to calculate a precise distance between the drill and the aforementioned interface and the closer the drill gets to the interface, the more forceful the haptic feedback may become. For example, there may be three levels of haptic feedback, the first level being a subtle vibration, the second level being a stronger vibration in combination with an intermittent kick and the third level, representing the drill being closest to the interface, may be a strongest vibration in combination with a quick set of repeated kicks. Details concerning the structure and operation of the haptic sleeve are described in detail below.

This monitoring and haptic feedback may continue until the desired shape of the prepared tooth is obtained and the clinician ends the drilling. However, should the clinician determine that further drilling is required to clear the diseased tissue, and this further drilling is beyond the interface, the clinician may override the haptic guidance by pressing a button on the haptic sleeve. Then, the preparation guidance may adapt to the additional drilling beyond the preparation guidance by defining a new removal volume that leaves a smaller prepared tooth and perhaps fits a smaller-sized tooth-wise end of a sleeve and in this case, monitoring and haptic guidance may resume.

After the tooth has been fully prepared, the optical imager may be used to ensure the desired tooth preparation has been achieved and then the image processing server 400 may select a desired prefabricated crown so as to best match the size and shape of the dental arch and mouth of the patient and may select a desired sleeve so as to have the desired tooth-wise end to match the prepared tooth and to have the desired crown-wise end to match the selected crown. The guidance console 420 may show the clinician which crown and sleeve have been selected. Thereafter, the clinician may cement the sleeve to the prepared tooth and the crown to the sleeve so as to implement the restoration.

Figure 26:
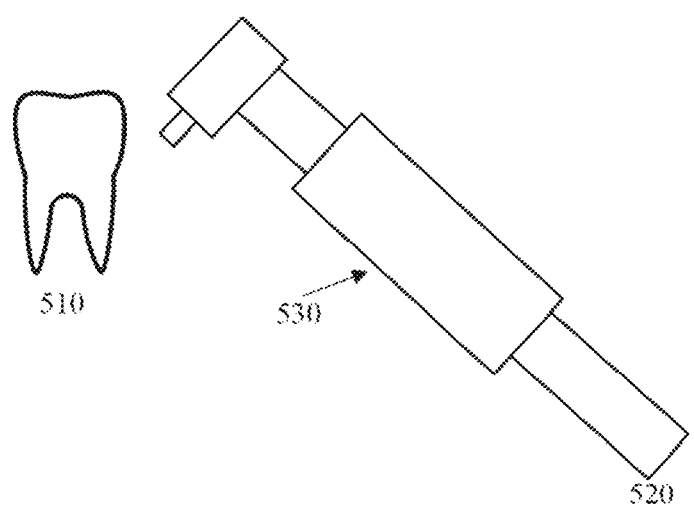
FIG. 26 is a schematic diagram illustrating a dental drill in combination with a haptic sleeve for providing haptic guidance in accordance with exemplary embodiments of the present invention.

FIG. 26 is a schematic diagram illustrating a dental drill in combination with a haptic sleeve for providing haptic guidance in accordance with exemplary embodiments of the present invention. As can be seen from this figure, the dental drill 520 may incorporate a haptic sleeve 530. The haptic sleeve 530 may be positioned around an exterior of the drill 520 such that the practitioner holds the drill 520 by the haptic sleeve 530 and therefore has increased sensation of the haptic feedback as the drill 520 is used to drill the affected tooth 510. In this respect, the haptic sleeve 530 forms a grip around a perimeter of a shaft of the dental drill 520. The haptic sleeve 530 may either be incorporated into the drill 520, in which case, the haptic sleeve 530 is powered by the drill 520, or the haptic sleeve 530 may be a device configured to receive an ordinary dental drill 520, in which case the haptic sleeve 530 provides its own power, for example, by the inclusion of a battery.

Figure 27:
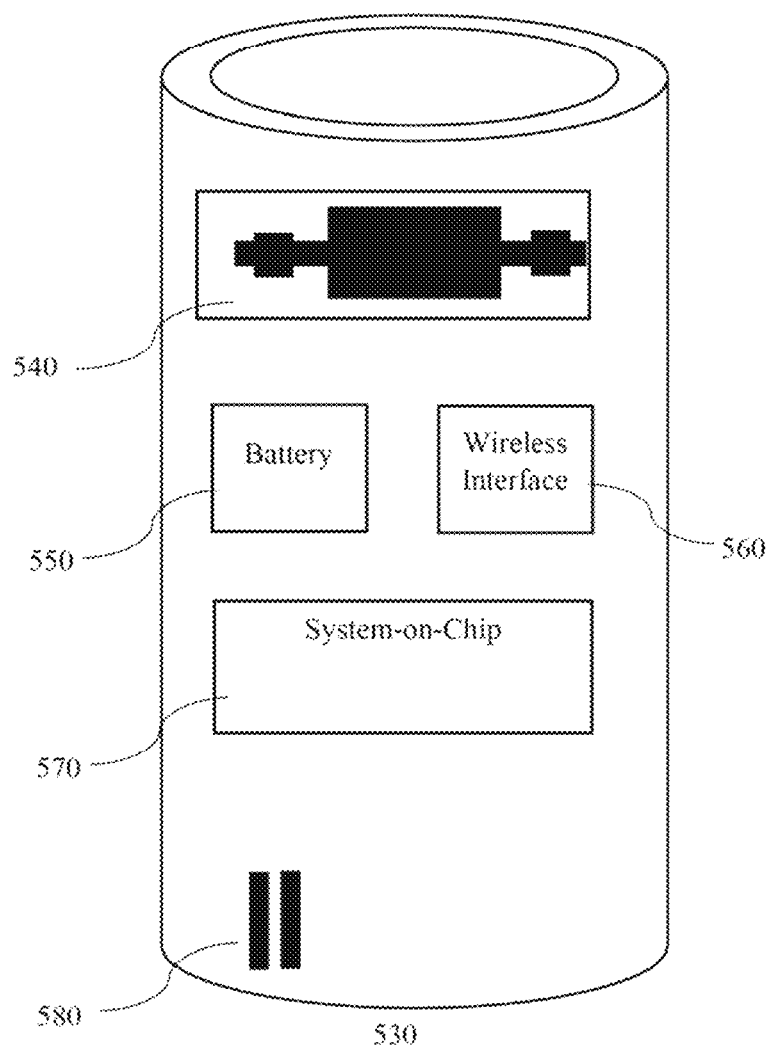
FIG. 27 is a detailed schematic diagram illustrating a haptic sleeve in accordance with exemplary embodiments of the present invention.

FIG. 27 is a detailed schematic diagram illustrating a haptic sleeve in accordance with exemplary embodiments of the present invention. As shown, the haptic sleeve 530 may be substantially pipe shaped so as to receive a dental drill 520 therein. The haptic sleeve 530 may include a haptic engine 540 for generating haptic feedback, a battery 550 for powering the haptic engine 540 and related components, a wireless interface 560 for receiving signals from the image processing server 400, and a system-on-chip 570 for controlling the operation of the haptic sleeve. The haptic sleeve 530 may further include docking contacts 580 so that the battery 550 may be recharged between uses of the haptic sleeve 530, with or without the drill disposed therein, when the haptic sleeve 530 is docked in a charging dock. The charging dock may also accommodate the aforementioned jaw immobilizer 460 for charging in a similar manner.

As discussed above, however, the haptic sleeve 530 may be permanently incorporated into the dental drill, in which case the battery 550, wireless interface 560, system-on-chip 570, and docking contacts 580 need not be included within the haptic sleeve 530 as it may receive power and control signals through the drill's 520 tether. In this case, the haptic engine 540 may be incorporated into a grip of the dental drill 520.

Although only a single haptic engine 540 is shown, it is to be understood that there may be multiple haptic engines 540 disposed, for example, radially, around the haptic sleeve 530. Each haptic engine 540 may include, for example, a weight that is disposed so as to freely slide along a rail. The weight may be magnetic and may either be a permanent magnet or may be a ferric material with one or more electromagnetic coils disposed around it. There may also be electromagnetic coils around each end of the rail so that electricity may be used to pull the weight to one side and then the other so as to create a haptic vibration as the electrical signal supplying power to the electromagnetic coils oscillates. The aforementioned kick sensation may be provided by activating at least one electromagnetic coils with a direct current signal so as to cause the weight to knock once against one side of the rail, rather than to vibrate continuously.

It is to be understood that the aforementioned knock sensation need not actually move the drill away from the tooth, but rather creates a directional sensation on the hand of the clinician who is holding the drill. Further, the sensation of vibration may be tuned by adjusting the length of the rail upon which the weight slides, the spacing of the electromagnetic coils and/or the oscillation of the driving signal so as to make the vibration of the haptic sleeve 540 feel substantially different from the natural vibration of the dental drill 530.

Chairside Milling

While exemplary embodiments of the present invention are generally described herein as using a pre-fabricated crown that may be polished to correct for the use of a crown that is somewhat larger than is ideal, it is to be understood that the embodiments described herein may make use of a modified chairside milling approach.

In traditional chairside milling, a crown, or other dental restoration, may be milled on-site from a solid block of ceramic, resin, zirconia, or other material using a 3D design expressed within a CAD/CAM file so that the patient does not have to leave the dentist's office for the number of days needed for the crown to be fabricated at the lab. This approach may be time consuming as chairside milling systems may take as much as an hour to fashion a crown from the solid block. While high-speed chairside milling systems are available and may be able to produce the desired crown within as little as ten minutes, these systems tend to be very expensive and so may not be suitably priced for widespread adoption.

Exemplary embodiments of the present invention may therefore adapt one or more of the approaches described herein with a partial chairside milling approach. Accordingly, rather than milling a crown, or other dental restoration, from the solid block, which may be substantially box or cube shaped, a prefabricated crown, that is shaped as described elsewhere within the instant application, may be milled into the shape of a smaller crown. Therefore, the chairside milling may be performed more quickly than if milling were to be performed from the solid block, even when using less expensive and more readily available chairside milling systems. Further, this approach may lead to less material waste and may provide less wear and tear on the milling machine and its burrs.

This approach of partial chairside milling from a substantially prefabricated crown, or other dental restoration, need not be limited to prefabricated crowns that are designed to interface with sleeves, as described herein, and may be readily applied to crowns that are intended to be adhered directly to a prepared tooth or implant abutment. Thus, chairside milling may be performed on a unit that is substantially crown-shaped, tooth-shaped or some other intermediate shape between a solid block and a finished crown or other dental restoration.

It is to be further understood that the shape of a prefabricated sleeve, as herein described, may be similarly customized by chairside milling.

Figure 35:
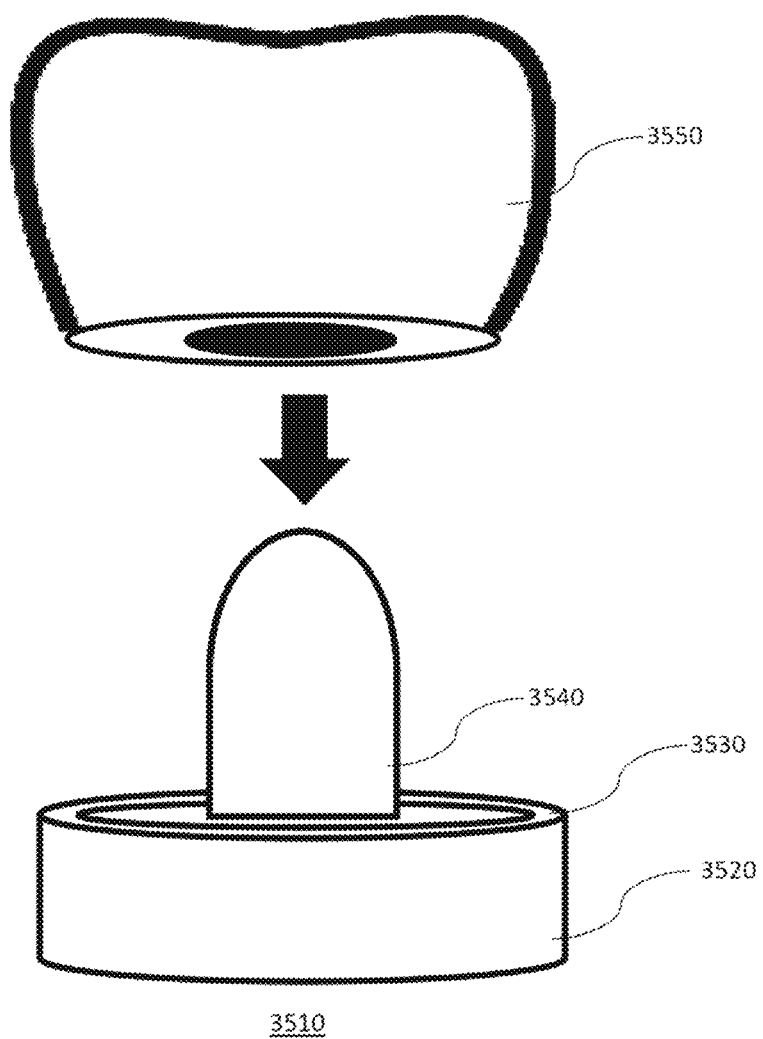
FIG. 35 is an exploded view illustrating a prefabricated crown being inserted into a milling chuck in accordance with exemplary embodiments of the present invention.

As it may be difficult to perform milling on a prefabricated crown, as described herein, owing to the shape of the prefabricated crown, exemplary embodiments of the present invention may utilize a special milling chuck to engage the prefabricated crown within the milling machine during the formation chairside milling. As can be seen from FIG. 35, which is an exploded view illustrating a prefabricated crown 3550 being inserted into a milling chuck 3510, the milling chuck 3510 may be adapted to accommodate the prefabricated crown 3550 by including a chuck base 3520 with a ridge 3530 disposed thereon. A center peg 3540 may be disposed onto the chuck base 3520 with the center peg 3540 being shaped to accommodate a central cavity of the prefabricated crown 3550. The prefabricated crown 3550 may be affixed to the milling chuck 3510 by friction between the interior of the prefabricated crown 3550 and the center peg 3540 as well as friction between the exterior of the prefabricated crown 3550 and the ridge 3530. The prefabricated crown 3550 may be alternatively or additionally affixed to the milling chuck 3510 by an adhesive disposed between the center peg 3540 and the prefabricated crown 3550. In this way, the prefabricated crown 3550 may be spun within the milling machine as it is further milled by one or more burrs of the milling machine so as to obtain the desired size and shape.

This modified chairside milling approach may be combined with the kit of prefabricated crowns described above with either any of the prefabricated crowns being suited for milling or additional items may be added to the kits to provide for more customizable crown shapes.

Colored Sleeves

Exemplary embodiments of the present disclosure relate to a kit of prefabricated sized and pigmented sleeves for use in conjunction with a set of prefabricated dental crown restorations, and a method for performing dental restorations using the same. According to this approach, a diseased or damaged tooth is prepared by drilling the affected tooth to a prepared state. Thereafter a selected prefabricated sleeve is installed onto the prepared tooth and a selected prefabricated crown is installed onto the sleeve. The sleeve is selected from a set of prefabricated sleeves in accordance with the size constraints of the prepared tooth and surrounding mouth as well as the desired color of the surrounding teeth, with a sleeve of a desired size being available for selection in one of a set of prefabricated pigmentation levels. The translucent and/or semi-opaque nature of the prefabricated crown allows for pigmentation of the selected sleeve to at least partially show through to an exterior surface of the crown thereby providing a desired pigmentation to the crown/sleeve combination that matches the surrounding teeth, without having to treat or otherwise apply coloring agents to the crown itself.

Figure 29A:
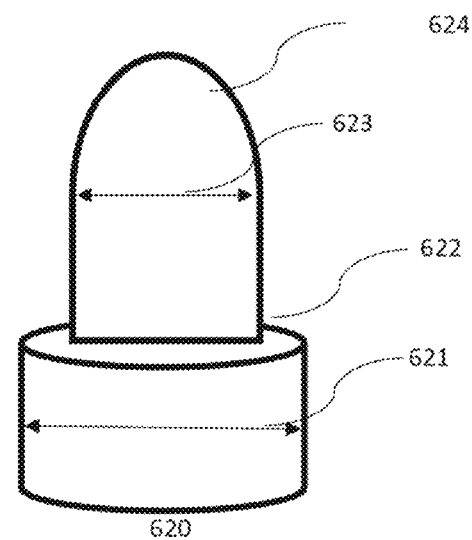
FIG. 29A is a detailed schematic view of a sleeve in profile/side view in accordance with exemplary embodiments of the present invention.
Figure 29B:
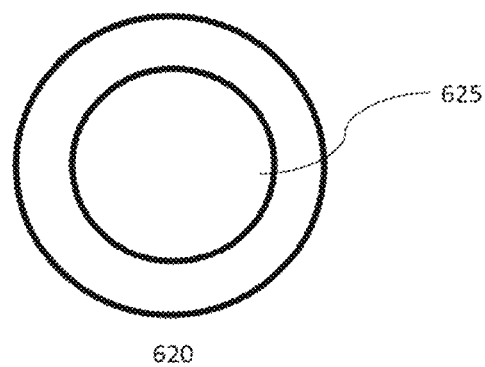
FIG. 29B is a detailed schematic view of a sleeve in bottom-up plan view in accordance with exemplary embodiments of the present invention.
Figure 30:
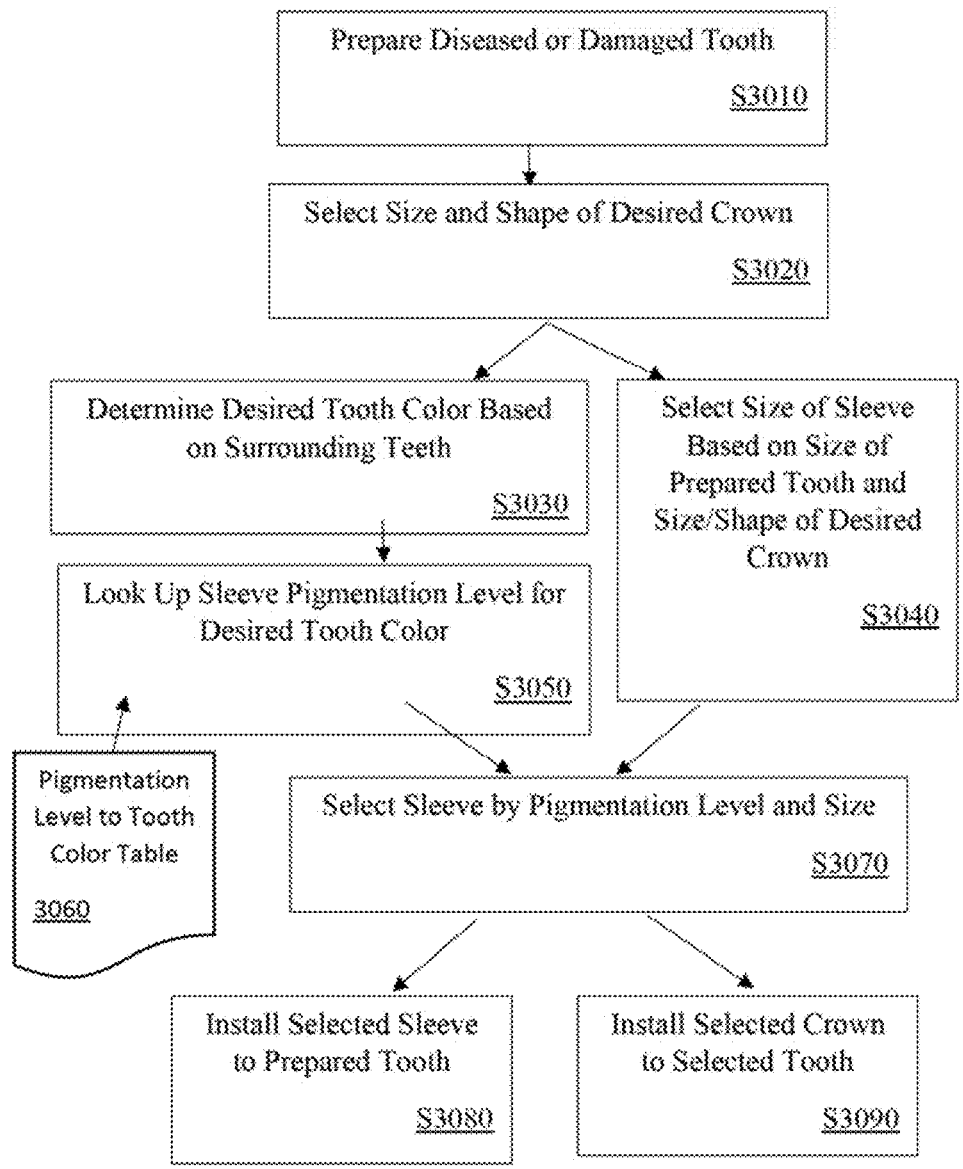
FIG. 30 is a flowchart illustrating a method for dental crown restoration using prefabricated pigmented sleeves in accordance with exemplary embodiments of the present invention.

FIG. 28 is a schematic diagram illustrating a system for performing dental crown restorations using prefabricated pigmented bushings/sleeves, FIGS. 29A and 29B includes detailed schematic views of a sleeve for use in the aforementioned dental crown restorations, and FIG. 30 is a flowchart illustrating a method for dental crown restoration using prefabricated pigmented sleeves in accordance with exemplary embodiments of the present invention.

The patient may have one or more affected teeth. An affected tooth is one in which there is disease or damage, such as decay or other structural impairments, that required dental restoration. In FIG. 28, a diseased or otherwise damaged tooth 600 is illustrated. While the affected tooth 600 is shown in FIG. 28 as including the tooth root, it is to be understood that the affected tooth 600 is within the mouth of the patient and the root is within the patient's gum line so that only a top portion of the affected tooth 600 is seen above the gumline. As is then shown in FIG. 30, the affected tooth 600 is then prepared (Step S3010). Preparation of the affected tooth 600 includes drilling away as much diseased and/or structurally damaged tooth volume as necessary to arrive at a shape of a prepared tooth 610 that is substantially peg-like. The prepared tooth 610 may have a flat or domed top and may have a cylindrical or somewhat conical base that gets wider at points closer to the tooth root. The clinician may prepare the affected tooth 600 so as to comply with a shape of the dental sleeves and/or bushings (referred to herein more simply as "sleeves" 620) that are part of the prefabricated sleeve kit, as will be described in more detail below.

Next, a size and shape of the desired crown 640 may be selected (Step S3020). This selection may be based on the size and spacing of the patient's mouth and the type of tooth that is being restored (e.g., incisor, cuspid, molar, etc.). The crown 640 of the desired size and shape may be selected from a kit of prefabricated crowns 640 of a plurality of different sizes and shapes. Each and every crown 640 of this kit may be substantially identical in color, being made of a translucent and/or semi-transparent material such as zirconium, or a different material such as nano-ceramics, lithium disilicate, etc. Each and every crown 640 of this kit may have a bottom surface hole/cavity of an identical size for accommodating each of the plurality of sleeves 620 of the sleeve kit, or the crowns 640 of the crown kit may have one of two, three, or four differently sized bottom surface holes/cavities for accommodating one of several differently sized sleeves 620. However, for the purpose of providing a simplified explanation, it will be assumed that each and every crown 640 of this kit may have a bottom surface hole/cavity of an identical size for accommodating each of the plurality of sleeves 620 of the sleeve kit.

After the desired crown 640 has been selected from the crown kit, a sleeve size may be selected from the sleeve kit according to the size of the prepared tooth 610, and/or the size/shape of the desired crown 640 (Step S3040). The sleeve kit may include a set of prefabricated sleeves, organized by size, particularly, by prepared tooth size. For example, the diameter of the prepared tooth (e.g., a largest diameter, a smallest diameter, and/or an average diameter) may be measured and a table may be referred to showing which sleeve 620 to select for a given diameter of prepared tooth. For a given sleeve size, the sleeve kit may include sleeves of multiple different pigmentation levels, as shown by element 660 of FIG. 28.

The desired final color of the crown restoration 640 may be determined by examining the surrounding teeth of the patient, for example, by referencing a set of printed colored cards against the patient's teeth or by using an electronic tooth color reader (Step S3030). A color table 3060 may then be referenced that provides a desired sleeve pigmentation level for a desired final color for the crown restoration 640 (Step S3050). As the crown 640 itself is translucent and/or semi-transparent, and as all crowns 640 of the crown kit are substantially identically colored, by using differently pigmented sleeves 660, some color of the sleeve 620 will show through the exterior surface of the dental restoration 640 so as to give the restored tooth a desired color. As the degree to which sleeve pigmentation may show through the final restoration may vary depending on the size and shape of the selected crown 640, the color table 3060 may take crown size and shape into account.

Once the desired sleeve size and pigmentation is known, a conforming prefabricated sleeve 620 may be selected from the sleeve kit that most closely matches the desired sleeve size and pigmentation (Step S3070).

The sleeve 620, as can be seen from FIG. 28, has an exterior surface and an interior surface (shown in broken lines). Each sleeve 620 of the sleeve kit may be constructed of a ceramic material, a plastic material, and/or a metal. The exterior surface of the sleeve 620 may be pigmented, as described above. This pigmentation may be painted, coated or glazed onto the exterior surface of the sleeve 620 during manufacture, or the material of the sleeve may be pigmented, after manufacture, according to the level of pigmentation for that particular sleeve 620.

The exterior surface of the sleeve 620 may be uniformly pigmented or the exterior surface of the sleeve may be differentially pigmented with portions of the sleeve 620 that are designed to be covered by more volume of crown 640 being more heavily pigmented than portions of the sleeve 620 that are designed to be covered by less volume of crown 640, so as to achieve a uniform pigmentation at a visible surface of the crown 640. For example, as the base of the sleeve 620 may be covered by a relatively thin section of crown 640 and the top of the sleeve 620 may be covered by a relatively thick section of crown 640, the sleeve 620 may be more heavily pigmented towards its top. However, this may be similarly the case for each level of pigmented sleeve 660 and so an average level of pigmentation may be higher for more heavily pigmented sleeves, even as each sleeve 620 itself may have a varied level of pigmentation.

The selected sleeve 620 may be installed onto the prepared tooth 610, for example, by mating the bottom opening of the sleeve to the prepared tooth 610 and applying bonding agent between the prepared tooth 610 and selected sleeve 620 and then curing the bonding agent (Step S3080). In this way, the selected sleeve 620 may be installed to the prepared tooth 610 so as to arrive at a sleeved tooth 630, as shown in FIG. 28.

The selected crown 640, which has an opening that substantially conforms to the shape of the top of the sleeve 620, may then be bonded to the sleeved tooth 630, for example, using a bonding agent that is substantially transparent/translucent (Step S3090). The substantially transparent/translucent bonding agent may be one that cures substantially transparent/translucent. However, where the bonding agent is known to cure partially transparent/translucent, this may be taken into account in the color table 3060 so as to use a more heavily pigmented sleeve 620 for a given final restoration color. It is to be understood, however, that the same bonding agent may be used for all such restorations, without regard to the desired color appearance of the finished restoration, so as to simplify installation and lessen the possibility of error. Moreover, the same bonding agent may be used to bond the sleeve 620 to the prepared tooth 610 so as to simplify installation, even as the color of the bonding agent used between the prepared tooth and the sleeve might not be relevant to the appearance of the finished restoration.

Installation may include applying the bonding agent between sleeved tooth 630 and crown 640 and curing the bonding agent once the crown 640 is in place so as to arrive at the crowned tooth 650 shown in FIG. 28. While the present invention is described in terms of bonding the sleeve 620 to the prepared tooth 610 before bonding the crown 640 to the sleeved tooth 630, this order may be reversed and the crown 640 may first be bonded to the sleeve 620 and then the crowned sleeve may be bonded to the prepared tooth 610.

While the shape of the sleeve 620 is shown in FIG. 28 as being substantially cylindrical, this shape is offered as an example. It is to be understood that the sleeve 620 may have a dome shape, a narrow dome shape (e.g., semi-ovaloid), a domed shape that narrows from base to top (narrowing dome), or a substantially cylindrical shape that is capped by a dome or narrow/narrowing dome. Thus, as shown in FIG. 29A, the sleeve 620 may have a smaller diameter towards the top 623 than towards the bottom 621. While the sleeve shape shown in FIG. 29A is discontinuous having an abrupt change of diameter 622 from a thick section to a thin section, this transition may be gradual so as to achieve one of the above-described shapes.

Also as shown in FIG. 29B, the underside of the sleeve 620 may include an opening hole 625 for receiving the prepared tooth 610.

Shaded Crowns

Exemplary embodiments of the present disclosure relate to an approach for performing a dental crown restoration in a single sitting. This may be performed at least in one of three ways. According to the first approach, the patient's tooth may be prepared by grinding the outer surface of the tooth to remove decayed or cracked portions of the tooth. This may result in a prepared tooth having a post-shape. Thereafter, an appropriately sized prefabricated sleeve may be filled with a dental cement and placed upon the prepared tooth. The dental cement may be cured through the sleeve using a light source. The sleeve may be at least partially translucent to light that may be used to cure the cement and so the cement may be easily cured through the sleeve. Thereafter, an appropriately sized prefabricated crown may be adhered to the sleeve using dental cement or some other adhesive, thereby creating a permanent dental restoration.

According to the second approach, the sleeve may be omitted and an appropriately sized prefabricated crown may be directly adhered to the prepared tooth.

According to the third approach, an entirety of the tooth may be extracted and an implant may be inserted through the gums and into the jawbone of the patient. An abutment may be placed on the dental implant and an appropriately sized prefabricated crown may be adhered to the abutment.

In each of these approaches, a prefabricated crown may be used. As it is not feasible to keep an unlimited number of differently sized and shaped prefabricated crowns on hand, exemplary embodiments of the present disclosure provide a method and process for sizing and fabricating a limited number of crowns that are well suited for use in the mouths of a majority of patients without requiring undue cutting or polishing of the prefabricated crown so that a patient may receive a single-visit dental restoration that is at least as good as a lab-made custom dental crown in terms of both function and aesthetics.

Figure 31:
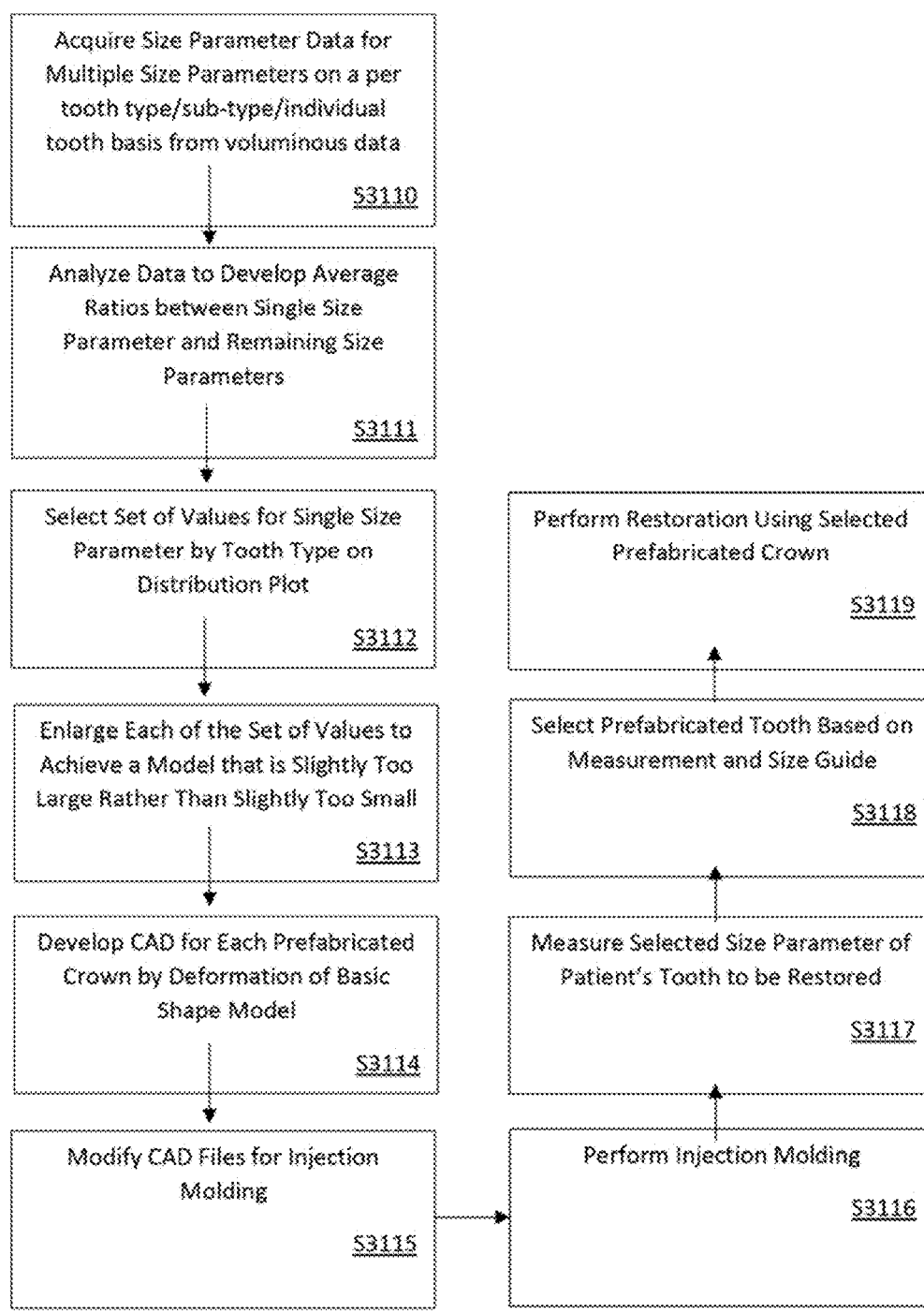
FIG. 31 is a flow chart illustrating a method for manufacturing a kit of prefabricated crowns and performing a dental restoration using the kit of prefabricated crowns in accordance with exemplary embodiments of the present invention.

FIG. 31 is a flow chart illustrating an approach for sizing and producing dental crowns for use in single-visit dental restorations in accordance with exemplary embodiments of the present disclosure. First, data of actual sizes of patient's teeth may be acquired (Step S3110). This data may be acquired on the basis of tooth type. As there are four types of human teeth (i.e., incisors, canines, premolars and molars), data may be separately acquired for each of these tooth types. Alternatively, data may be acquired separately on the basis of tooth sub-type including central incisor, lateral incisor, canine, first premolar, second premolar, first molar, second molar, and third molar or wisdom teeth. Alternatively, data may be acquired separately on the basis of individual teeth.

In acquiring size data for each tooth type/subtype/individual tooth, various size parameters may be measured. These size parameters may include: (1) the buccal-lingual distance (e.g., the thickness of the tooth from buccal to lingual), (2) the mesial-distal distance (e.g., the width of the tooth from mesial to distal), (3) the occlusal distance (e.g., the height of the tooth measured from the cervix to the cusps), and (4) the cervical margin (e.g., the circumference of the tooth at the cervix). However, this list is not intended to be exhaustive and other size parameters may be used.

This data may be acquired automatically from analyzing intra-oral images or digital scans of physical shape models (e.g., taken from impressions). Computer vision techniques may be used to identify key landmarks for each tooth in 3D space, such as the buccal edge, the lingual edge, the mesial edge, the occlusal edge, the cervical margin, the cusps, etc. and measurements may be made, and data collected, electronically.

After the data has been acquired, the data may be analyzed to develop average ratios between each of these size parameters (Step S3111). This may be performed by looking at the size parameters of each tooth and determining a ratio of each size parameter to a single size parameter. For example, the chosen single size parameter may be the mesial-distal distance. In this example, a ratio of mesial-distal distance to each of the other size parameters may be measured. Then, for each tooth of the data, the same set of ratios may be determined and averaged together to determine an average ratio between mesial-distal distance to each of the other size parameter. For example, an average ratio between mesial-distal distance to buccal-lingual distance may be gleaned, an average ratio between mesial-distal distance to occlusal distance may be gleaned, an average ratio between mesial-distal distance to cervical margin may be gleaned. By finding each of these average ratios over a very large data set (for example, from thousands of intra-oral images), tooth size may be understood by using only this selected single size parameter (here, mesial-distal distance, although it is to be understood that any of the size parameters may be used as the selected single size parameter). As these average ratios are calculated on a per-tooth basis (or per tooth type or tooth sub-type), the size of any given tooth may be characterized by only its single size parameter (e.g., the mesial-distal distance) and the known ratios to the other average size parameters.

Figure 32:
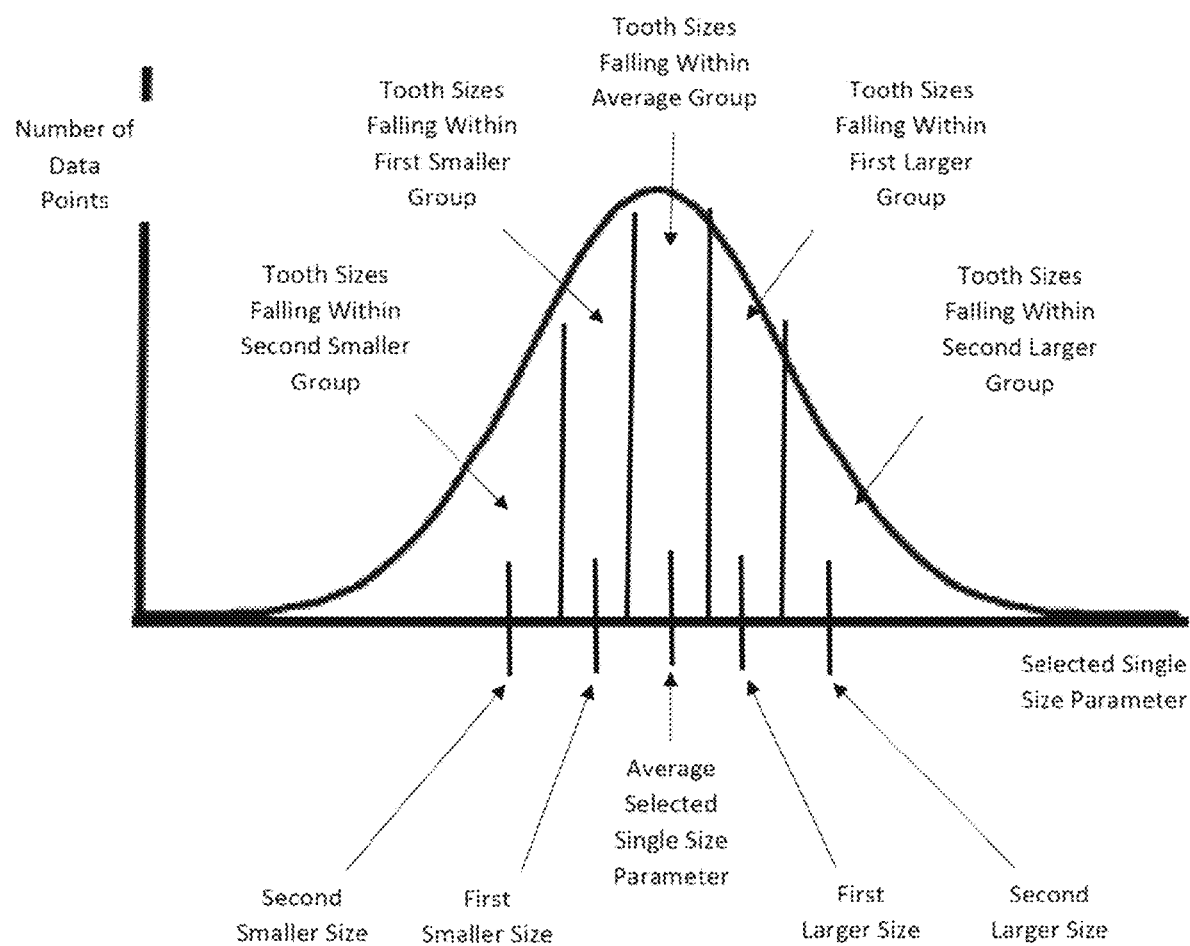
FIG. 32 is a graph illustrating an approach for determining sizes for prefabricated crowns according to the size of teeth of a distribution of subjects in accordance with exemplary embodiments of the present invention.

Then, for each tooth type/subtype/individual tooth, the selected single size parameter may be plotted for all of the data. This may create a Gaussian distribution of the data, as may be seen from FIG. 32 which is a plot of the selected single size parameter (here, the mesial-distal distance). As can be seen from this graph, the average value for the selected single size parameter may be found at the center of the Gaussian distribution. From there, one or more additional sizes may be selected. As shown in this example, two additional larger sizes and two additional smaller sizes are selected so as to arrive at 5 total sizes. Each size has an associated group and each data point of the tooth size data that falls within one of these 5 groups.

The placement of the additional sizes may be made based on a predetermined number of standard deviations from the average. For example, the first smaller size may be selected as −1 standard deviation from the average, the second smaller size may be selected as −2 standard deviations from the average, the first larger size may be selected as +1 standard deviation from the average, and the second larger size may be selected as −2 standard deviations from the average. Thus, a given number of values (here, 5) for the selected single size parameter (here, mesial-distal distance) may be selected based on a distribution plot of the data by tooth type/subtype/individual tooth (Step S3112).

It is understood that as it is better for a prefabricated crown to be slightly bigger than ideal than to be slightly smaller than ideal (as a crown that is a little too large can be trimmed or polished), each of the selected values may be enlarged (Step S3113). Therefore, the average group tooth size (measured by the selected single size parameter) may be slightly larger than the average value, the first smaller size may be slightly larger than −1 standard deviation from average, the second smaller size may be slightly larger than −2 standard deviations from average, the first larger size may be slightly larger than +1 standard deviation from average, and the second larger size may be slightly larger than +2 standard deviations from average. Enlargement may be based on a fixed amount (e.g., each value is enlarged by 2 mm) or enlargement may be based on the distribution curve (e.g., each value is enlarged by 0.2 standard deviations).

Alternatively, each crown may be enlarged by a fixed percentage of size. For example, each crown may be enlarged by 2%.

Next, for each tooth type/subtype/individual tooth, the enlarged selected values of the single selected size parameter may be used to develop a CAD image for a set of crowns to be prefabricated (Step S3114). This may be performed by starting with the enlarged selected value (which may be, for example, a mesial-distal distance) and using the set of average ratios to determine a full set of corresponding size parameters for each enlarged selected values of the single selected size parameter. For example, the average ratio of mesial-distal distance to buccal-lingual distance may be used to calculate a buccal-lingual distance that corresponds to the average selected size parameter. This may be performed for all of the selected values and all of the size parameters so for each enlarged selected size value (e.g., all 5) there is a fill set of size parameters that have been calculated using the set of average ratios.

In constructing the CAD images, the size parameters may be used to perform a rigid or elastic deformation on a basic shape model. There may be one basic shape model created for each tooth type/subtype/individual tooth. The basic shape model may be constructed by digitally averaging the topography of a large set of images of teeth of the particular tooth type/subtype/individual tooth captured from intra-oral scans of a large number of subjects or digital scans of physical shape models (e.g., taken from impressions). This process may be performed using finite element analysis (FEA) using a computer application such as SOLID-WORKS, a solid modeling computer aided design (CAD) program published by Dassault Systèmes. The result of this process is to obtain a basic shape model that includes smooth cusps and pits.

Thereafter, each of the constructed CAD models may be modified for injection molding (Step S3115). This may include automatically editing the CAD model so as to change features that would be incompatible with certain injection molding techniques. These edits may include: (1) in corner design, making an outside radius of curvature one wall thickness larger than an inside radius of curvature so as to maintain a constant wall thickness through the corners, (2) convert abrupt steps to curves, (3) edit angles to better alight walls parallel to a direction of mold separation, (4) reduce or remove concavities that may make the cervical diameter smaller than a diameter of the crown closer to the cusps, and (5) edit the geometry of the cusps and pits of the crown to make sure pits do not widen in a direction towards the cervix.

Upon editing the CAD models to account for injection molding concerns, the crowns may be manufactured, in each size, for example, by injection molding (Step S3116). Alternatively, other approaches may be used to manufacture the crowns such as by 3D printing, milling, etc., and where injection molding is not used, the step of modifying the CAD model for injection molding may be omitted.

Figure 33:
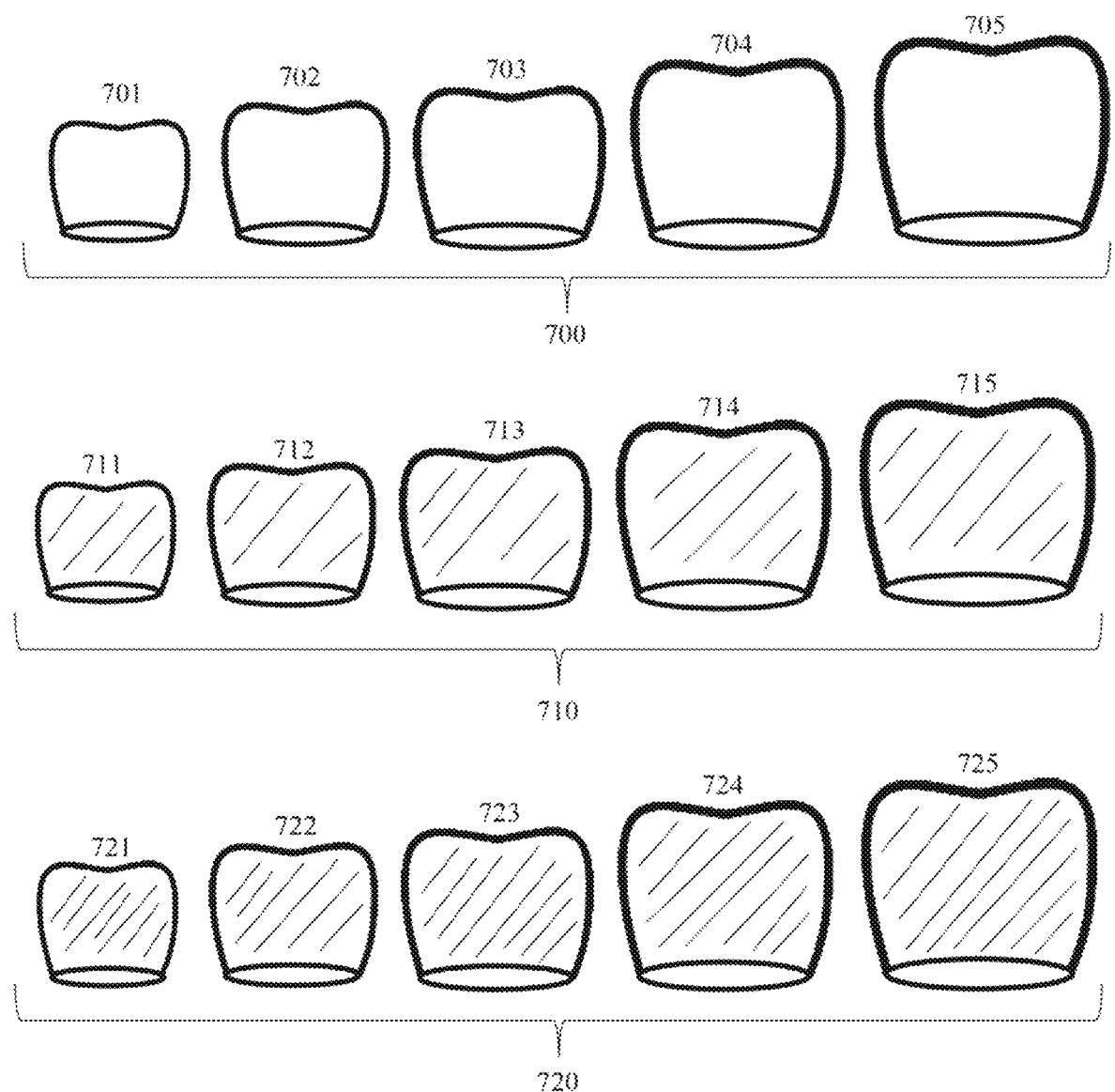
FIG. 33 is a diagram illustrating prefabricated crown sets for restoration of molars in accordance with exemplary embodiments of the present invention.

The process of manufacturing the crowns in all sizes may be repeated using different materials having different levels of pigment so that the end result, as may be seen from FIG. 33, is a kit of prefabricated crowns in a plurality of different sizes and pigment levels. FIG. 33 shows such a kit produced for use in restoring molars, however, similar kits may also be manufactured for other types of teeth.

As can be seen from FIG. 33, there may be multiple sets of prefabricated crowns for one tooth type, here shown as molars. A first set 700 may be prefabricated for a first shade level. Within this first set 700, there may be an average sized crown 703, a crown of a first smaller size 702, a crown of a second smaller size 701, a crown of a first larger size 704 and a crown of a second larger size 705, with each crown 701-705 of the first set 700 being of the first shade level.

A second set of prefabricated crowns 710 may be made with a second shade level that is darker than the first shade level. Within this second set 710, there may be an average sized crown 713, a crown of a first smaller size 712, a crown of a second smaller size 711, a crown of a first larger size 714 and a crown of a second larger size 715, with each crown 711-715 of the second set 710 being of the second shade level.

A third set of prefabricated crowns 720 may be made with a third shade level that is darker than the first and second shade levels. Within this third set 720, there may be an average sized crown 723, a crown of a first smaller size 722, a crown of a second smaller size 721, a crown of a first larger size 724 and a crown of a second larger size 725, with each crown 721-725 of the third set 720 being of the third shade level.

It is to be further understood that there may be additional sets of prefabricated crowns with additional shades, and that such sets may be made for every tooth type.

In this way, the kit of crowns may be prefabricated. Then, when a patient presents at the office of a dentist for a dental restoration, the selected size parameter, for example, the mesial-distal distance, may be measured in the patient for the tooth being restored (Step S3117). A prefabricated tooth may then be selected from the kit based on the measured selected size parameter (Step S3118), for example, using a size guide that references ranges of the selected size parameter for each prefabricated crown size. This step may alternatively be performed automatically by taking an intra-oral scan of the patient's mouth, measuring the mesial-distal distance of the affected tooth, and referencing a size guide table to select a particular prefabricated crown size and display the selected size to the dentist.

Also, at this step, the pigment of the patient's teeth may be assessed, either by using color cards or automatically by analyzing the intra-oral scan taken when determining the crown size to use. As the kit of prefabricated crowns may only include a particular number of different pigments, for example, 3, 4, or 5 different pigments, a closest available pigment may be selected from among the prefabricated crowns of the kit. Alternatively, the kit might only include prefabricated crowns of one particular color and the pigment of the crown may be adapted by applying a coloring agent to the prefabricated crown.

After the desired prefabricated crown has been selected from the kit, the dentist may perform the restoration using the selected crown (Step S3119). This may include, for example, preparing the patient's tooth by grinding away the affected tissue until the tooth has a peg-shape, affixing a sleeve to the prepared tooth, and then cementing the prefabricated crown to the sleeve. Alternatively, the sleeve may be omitted and the selected prefabricated tooth may be cemented directly to the prepared tooth. Alternatively, the tooth may be removed, an implant may be inserted into the patient's mouth, an abutment may be mounted on the implant, and the selected prefabricated crown may be affixed to the abutment.

Figure 34:
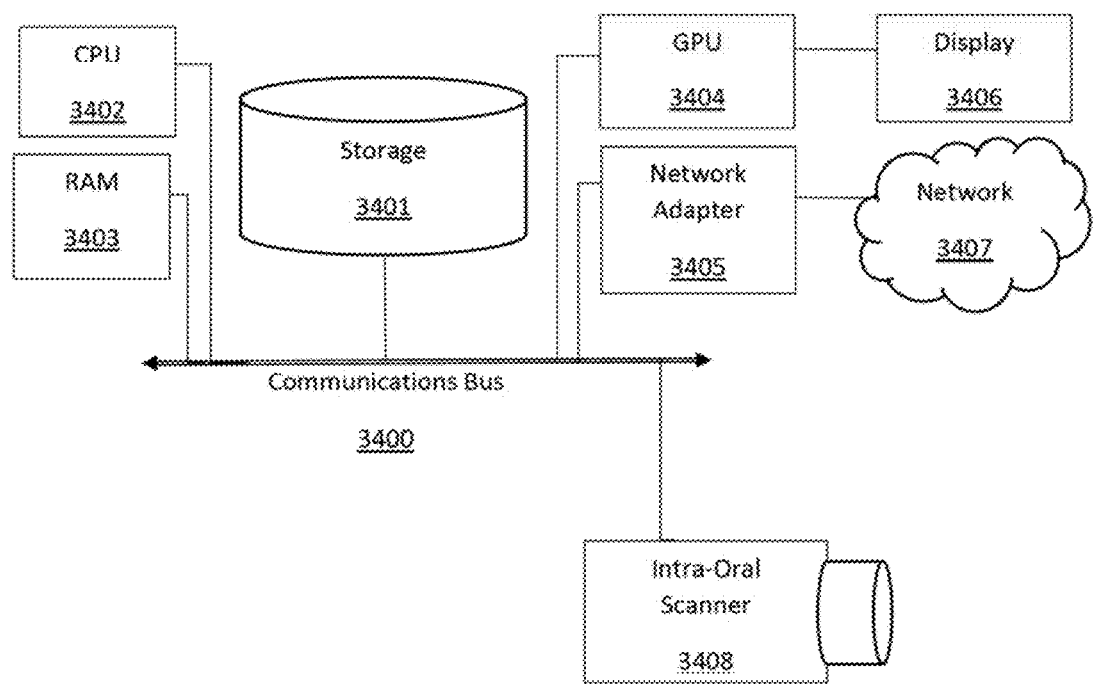
FIG. 34 is a diagram illustrating a computer system for manufacturing a kit of prefabricated crowns and performing a dental restoration using the kit of prefabricated crowns in accordance with exemplary embodiments of the present invention.

As mentioned above, the process of selecting a prefabricated tooth may be performed automatically from an intra-oral scan using an arrangement such as the computer system depicted in FIG. 34. An intra-oral scanner 3408 may be used to acquire the intra-oral scan. The intra-oral scanner 3408 may be connected to a computer system either by a wired connection, for example, using a USB cable, or by a wireless connection such as Bluetooth or WiFi. The computer system may then analyze the intra-oral scan using a CPU 3402 in conjunction with RAM 3403 and other computer components which may all be connected to each other along one or more communications busses 3400. The computer system may analyze the intra-oral scan to determine crown size and pigment, as described above, using a computer vision application that is stored in a storage unit 3401 such as an SSD or HDD. The aforementioned size guide table may also be stored within this, or another, storage unit 3401. The computer system may display a name or reference number of the selected prefabricated crown using a GPU 3404 and display device 3406. The computer system may additionally include a network adapter 3405 to connect to a computer network 3407 such as a local area network LAN or a wide area network WAN such as the Internet so that, for example, the selected prefabricated crown may be displayed on a connected device, such as a small display incorporated into the intra-oral scanner or a smartphone/smartwatch carried by the dentist.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A dental restoration device, comprising:
   a sleeve having an exterior surface and an interior pocket that is at least partially filled with a dental cement; and
   a crown having an exterior surface and an interior surface that is mated to the exterior surface of the sleeve and bonded thereto by an adhesive disposed between the exterior surface of the sleeve and the interior surface of the crown,
   wherein a thickness of the crown at an occlusal side thereof is greater than a thickness of the sleeve at an occlusal side thereof,
   wherein the sleeve and the crown are each pre-fabricated with respect to a preparation of a tooth upon which the dental restoration device is to be installed and configured to be installed on the prepared tooth,
   wherein the crown is a permanent crown, and
   wherein the dental cement is a light-curing cement and the sleeve is at least partially translucent to light.

2. The dental restoration device of claim 1, wherein the exterior surface of the crown has a shape including at least one cusp and the interior surface of the crown has a shape that is inverted with respect to the shape of the exterior surface of the crown.

3. The dental restoration device of claim 1, wherein the crown includes a polymer with ceramic and/or glass particles suspended therein.

4. The dental restoration device of claim 1, wherein the sleeve includes a polymer.

5. The dental restoration device of claim 1, wherein the dental cement has a high Young's modulus within a range of 2 and 60 GPa in a cured state.

6. The dental restoration device of claim 1, wherein the sleeve has a high Young's modulus within a range of 2 and 60 GPa.

7. The dental restoration device of claim 1, wherein both the crown and the sleeve are non-porous.

8. A dental restoration device, comprising:
   a sleeve having an exterior surface and an interior pocket that is at least partially filled with a dental cement; and
   a crown having an exterior surface and an interior surface that is mated to the exterior surface of the sleeve and bonded thereto by an adhesive disposed between the exterior surface of the sleeve and the interior surface of the crown,
   wherein a gingival end of the crown is substantially co-planar with a gingival end of the sleeve,
   wherein the sleeve and the crown are each pre-fabricated with respect to a preparation of a tooth upon which the dental restoration device is to be installed and configured to be installed on the prepared tooth,
   wherein the crown is a permanent crown, and
   wherein the dental cement is a light-curing cement and the sleeve is at least partially translucent to light.

9. The dental restoration device of claim 8, wherein the exterior surface of the crown has a shape including at least one cusp and the interior surface of the crown has a shape that is inverted with respect to the shape of the exterior surface of the crown.

10. The dental restoration device of claim 8, wherein the crown includes a polymer with ceramic and/or glass particles suspended therein.

11. The dental restoration device of claim 8, wherein the sleeve includes a polymer.

12. The dental restoration device of claim 8, wherein the dental cement has a high Young's modulus within a range of 2 and 60 GPa in a cured state.

13. The dental restoration device of claim 8, wherein the sleeve has a high Young's modulus within a range of 2 and 60 GPa.

14. The dental restoration device of claim 8, wherein both the sleeve and the crown are non-porous.

15. A dental restoration device, comprising:
    a sleeve having an exterior surface and an interior pocket that is at least partially filled with a dental cement; and
    a crown having an exterior surface and an interior surface that is mated to the exterior surface of the sleeve and bonded thereto by an adhesive disposed between the exterior surface of the sleeve and the interior surface of the crown,
    wherein a thickness of the crown at an occlusal side thereof is greater than a thickness of the sleeve at an occlusal side thereof,
    wherein the sleeve and the crown are each pre-fabricated with respect to a preparation of a tooth upon which the dental restoration device is to be installed and configured to be installed on the prepared tooth,
    wherein the sleeve is pre-fabricated as rigid and having a fixed shape, and
    wherein the dental cement is a light-curing cement and the sleeve is at least partially translucent to light.

16. The dental restoration device of claim 15, wherein the exterior surface of the crown has a shape including at least one cusp and the interior surface of the crown has a shape that is inverted with respect to the shape of the exterior surface of the crown.

17. The dental restoration device of claim 15, wherein the crown includes a polymer with ceramic and/or glass particles suspended therein.

18. The dental restoration device of claim 15, wherein the sleeve includes a polymer.

19. The dental restoration device of claim 15, wherein the dental cement has a high Young's modulus within a range of 2 and 60 GPa in a cured state.

20. The dental restoration device of claim 15, wherein the sleeve has a high Young's modulus within a range of 2 and 60 GPa.

21. A dental restoration device, comprising:
    a sleeve having an exterior surface and an interior pocket that is at least partially filled with a dental cement; and
    a crown having an exterior surface and an interior surface that is mated to the exterior surface of the sleeve and bonded thereto by an adhesive disposed between the exterior surface of the sleeve and the interior surface of the crown,
    wherein a gingival end of the crown is substantially co-planar with a gingival end of the sleeve,
    wherein the sleeve and the crown are each pre-fabricated with respect to a preparation of a tooth upon which the dental restoration device is to be installed and configured to be installed on the prepared tooth, wherein the sleeve is pre-fabricated as rigid and having a fixed shape, and wherein the dental cement is a light-curing cement and the sleeve is at least partially translucent to light.

22. The dental restoration device of claim 21, wherein the exterior surface of the crown has a shape including at least one cusp and the interior surface of the crown has a shape that is inverted with respect to the shape of the exterior surface of the crown.

23. The dental restoration device of claim 21, wherein the crown includes a polymer with ceramic and/or glass particles suspended therein.

24. The dental restoration device of claim 21, wherein the sleeve includes a polymer.

25. The dental restoration device of claim 21, wherein the dental cement has a high Young's modulus within a range of 2 and 60 GPa in a cured state.

26. The dental restoration device of claim 21, wherein the sleeve has a high Young's modulus within a range of 2 and 60 GPa.

\* \* \* \* \*